(12) United States Patent
Campbell et al.

(10) Patent No.: US 10,500,081 B2
(45) Date of Patent: Dec. 10, 2019

(54) TRIPLE ACTION ORTHOTIC ANKLE JOINT AND METHODS

(71) Applicant: Becker Orthopedic Appliance Company, Troy, MI (US)

(72) Inventors: James Campbell, Clarkston, MI (US); Nicholas LeCursi, Saline, MI (US); Nicholas Zalinski, Macomb Township, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 726 days.

(21) Appl. No.: 14/738,212

(22) Filed: Jun. 12, 2015

(65) Prior Publication Data

US 2016/0361189 A1 Dec. 15, 2016

(51) Int. Cl.
*A61F 5/01* (2006.01)

(52) U.S. Cl.
CPC .......... *A61F 5/0127* (2013.01); *A61F 5/0125* (2013.01); *A61F 2005/0179* (2013.01); *A61F 2240/001* (2013.01)

(58) Field of Classification Search
CPC .... A61F 5/0127; A61F 5/0123; A61F 5/0125; A61F 5/0102; A61F 5/0118; A61F 5/013; A61F 5/0111; A61F 5/01; A61F 5/0113; A61F 2005/0165; A61F 2005/0167; A61F 2005/0169; A61F 2005/0162; A61F 2005/0179; A61F 2005/0174; A61F 2005/0134; A61F 2005/0137; A61F 2005/0146; A61F 2005/0151;

(Continued)

(56) References Cited

U.S. PATENT DOCUMENTS 5,044,360 A 9/1991 Janke
5,176,623 A 1/1993 Stetman et al.
(Continued)

OTHER PUBLICATIONS

International Searching Authority (ISA/US), International Search Report and Written Opinion, International Application No. PCT/US2016/037010, dated Sep. 27, 2016.
(Continued)

*Primary Examiner* — Alireza Nia
*Assistant Examiner* — Rachel A Berezik
(74) *Attorney, Agent, or Firm* — Hinshaw & Culbertson LLP

(57) ABSTRACT

In one aspect, an improved ankle joint device provides two stages of dorsiflexion resistance biasing a first splint member (or other attachment member that follows the angular displacement of a wearer's lower leg or foot) against dorsiflexion movement within an active angular range of dorsiflexion, corresponding to second and third rocker phases of a wearer's gait; in addition to a phase of plantarflexion resistance biasing the first splint/attachment member against plantarflexion movement within an active angular range of plantarflexion, corresponding to a first rocker phase. In another aspect, an equilibrium or neutral angle between a wearer's foot and tibia at which the device applies no biasing forces is adjustable by adjusting the angle at which a second splint/attachment member is fixed relative to a joint body. Typically, the second splint member is secured to a wearer's lower leg, and the first splint member is secured to a wearer's foot.

25 Claims, 21 Drawing Sheets

(58) Field of Classification Search
CPC ...... A61F 2005/0153; A61F 2005/0155; A61F 2005/0158; A61F 2005/0197; A61F 2/64; A61F 2/642; A61F 2/644; A61F 2/646; A61F 2/6607; A61F 2005/0195
See application file for complete search history.

(56) References Cited

U.S. PATENT DOCUMENTS

| | | | |
|---|---|---|---|
| 5,399,149 A * | 3/1995 | Frankowiak | A61F 5/0125 |
| | | | 16/326 |
| 5,445,603 A | 8/1995 | Wilkerson | |
| 5,486,157 A | 1/1996 | DiBenedetto | |
| 5,571,077 A | 11/1996 | Klearman et al. | |
| 5,788,618 A | 8/1998 | Joutras | |
| 5,902,259 A | 5/1999 | Wilkerson | |
| 6,036,665 A | 3/2000 | Towsley | |
| 6,056,712 A | 5/2000 | Grim | |
| 6,129,690 A | 10/2000 | Hamlin et al. | |
| 6,299,587 B1 | 10/2001 | Birmingham | |
| 6,319,218 B1 | 11/2001 | Birmingham | |
| 6,488,644 B1 | 12/2002 | Ostrom et al. | |
| 6,752,774 B2 | 6/2004 | Townsend et al. | |
| 6,824,523 B2 | 11/2004 | Carlson | |
| 6,860,864 B2 | 3/2005 | Meyer | |
| 7,018,350 B2 | 3/2006 | Hinshon | |
| 7,101,346 B1 | 9/2006 | Davis | |
| 7,201,728 B2 | 4/2007 | Sterling | |
| 7,235,058 B2 * | 6/2007 | Doty | A61F 5/0123 |
| | | | 602/16 |
| 7,691,076 B2 | 4/2010 | Castro | |
| 7,740,602 B2 | 6/2010 | Christensen | |
| 7,766,851 B2 | 8/2010 | Lindh et al. | |
| 7,846,120 B2 | 12/2010 | DeToro et al. | |
| 7,878,993 B2 | 2/2011 | Agrawal et al. | |
| 8,075,633 B2 | 12/2011 | Herr et al. | |
| 8,114,042 B2 | 2/2012 | Klotz et al. | |
| 8,221,341 B1 | 7/2012 | Al-Oboudi | |
| 8,251,935 B2 | 8/2012 | Bonutti et al. | |
| 8,287,477 B1 | 10/2012 | Herr et al. | |
| 8,298,294 B2 | 10/2012 | Kaltenborn et al. | |
| 8,313,451 B2 | 11/2012 | Cox | |
| 8,376,971 B1 | 2/2013 | Herr et al. | |
| 8,382,694 B2 | 2/2013 | Wenger | |
| 8,444,583 B2 | 5/2013 | Phillips | |
| 8,454,543 B2 | 6/2013 | Skahan et al. | |
| 8,465,445 B2 | 6/2013 | George | |
| 8,474,666 B2 | 7/2013 | Vitillo et al. | |
| 8,480,604 B2 | 7/2013 | Messer | |
| 8,480,760 B2 | 7/2013 | Hansen et al. | |
| 8,491,511 B2 | 7/2013 | Gentz et al. | |
| 8,500,668 B2 | 8/2013 | Siegler et al. | |
| 8,512,269 B1 | 8/2013 | Stano et al. | |
| 8,512,415 B2 | 8/2013 | Herr et al. | |
| 8,538,570 B2 | 9/2013 | Stanhope et al. | |
| 8,551,029 B1 | 10/2013 | Herr et al. | |
| 8,551,169 B2 | 10/2013 | Fitz et al. | |
| D693,471 S | 11/2013 | Bradshaw | |
| 8,578,634 B1 | 11/2013 | Nguyen et al. | |
| 8,585,708 B2 | 11/2013 | Fitz et al. | |
| 8,591,446 B2 | 11/2013 | Helm | |
| 8,597,369 B2 | 12/2013 | Hansen et al. | |
| 8,696,764 B2 | 4/2014 | Hansen et al. | |
| 8,728,171 B2 | 5/2014 | Kaltenborn et al. | |
| 8,734,371 B2 | 5/2014 | Robertson | |
| D706,942 S | 6/2014 | Bradshaw | |
| 8,753,275 B2 | 6/2014 | Najafi et al. | |
| D708,343 S | 7/2014 | Davis | |
| 8,771,211 B2 | 7/2014 | Bonutti et al. | |
| 8,790,282 B2 | 7/2014 | Jung et al. | |
| 8,808,214 B2 | 8/2014 | Herr et al. | |
| 8,814,868 B2 | 8/2014 | Janna et al. | |
| 8,821,588 B2 | 9/2014 | Latour | |
| 8,828,095 B2 | 9/2014 | Mosler et al. | |
| 8,838,263 B2 | 9/2014 | Sivak et al. | |
| 8,852,292 B2 | 10/2014 | Ragnarsdottir et al. | |
| 8,858,482 B2 | 10/2014 | Ingimundarson et al. | |
| 8,870,801 B2 | 10/2014 | Tomiyama et al. | |
| 2001/0051780 A1 | 12/2001 | Birmingham | |
| 2002/0188238 A1 | 12/2002 | Townsend et al. | |
| 2004/0015112 A1 | 1/2004 | Salutterback et al. | |
| 2006/0206043 A1 | 9/2006 | Yakimovich et al. | |
| 2007/0049858 A1 | 3/2007 | Agrawal et al. | |
| 2007/0219475 A1 | 9/2007 | Bonutti et al. | |
| 2008/0255489 A1 | 10/2008 | Genda et al. | |
| 2010/0076346 A1 | 3/2010 | Abel et al. | |
| 2010/0185301 A1 | 7/2010 | Hansen et al. | |
| 2011/0251539 A1 * | 10/2011 | Gentz | A61F 5/0127 |
| | | | 602/16 |
| 2012/0016493 A1 | 1/2012 | Hansen et al. | |
| 2012/0209163 A1 | 8/2012 | Phillips | |
| 2013/0006386 A1 | 1/2013 | Hansen et al. | |
| 2013/0245524 A1 | 9/2013 | Schofield | |
| 2013/0281898 A1 | 10/2013 | Cropper et al. | |
| 2013/0296754 A1 * | 11/2013 | Campbell | A61F 5/0123 |
| | | | 602/16 |
| 2013/0345611 A1 | 12/2013 | Phillips | |
| 2014/0066829 A1 | 3/2014 | Drillio | |
| 2014/0088729 A1 | 3/2014 | Herr et al. | |
| 2014/0276304 A1 | 9/2014 | Dollar et al. | |
| 2014/0276316 A1 | 9/2014 | Bradshaw | |
| 2015/0216701 A1 | 8/2015 | Semsch et al. | |
| 2016/0151190 A1 | 6/2016 | Lurssen et al. | |

OTHER PUBLICATIONS

Fior & Gentz GmbH, Neuro Swing System Ankle Joint; product manual published Oct. 2012; pp. 1-16 (German), pp. 17-31 (English), Fior & Gentz GmbH, Luneburg, Germany.

* cited by examiner

TRIPLE ACTION ORTHOTIC ANKLE JOINT AND METHODS

FIELD OF THE INVENTION

The present invention relates to devices that assist a wearer's ankle joint during walking, such as ankle-foot orthoses (AFO) and knee-ankle-foot orthoses (KAFO). More particularly, it relates to devices that assist the wearer's ankle joint in resisting dorsiflexion and plantarflexion of the user's foot.

BACKGROUND

Various types of devices exist for orthotic management of lower limb biomechanical deficits. For example, one type of orthotic ankle joint device includes a joint component with a splint mounting and a stirrup component that pivots relative to the joint component, providing resistance to dorsiflexion and plantarflexion pivotal movements away from a relatively central equilibrium (also termed "neutral" herein) ankle alignment angle of the wearer's lower leg with respect to the ankle, at which angle there is no net biasing force on the device.

To adapt an orthotic ankle joint device to the physiology and condition of the individual wearer, it is advantageous to adjust or tune the equilibrium ankle alignment angle, plantarflexion resist torque, and dorsiflexion resist torque. In addition, it may be advantageous to alter the angle versus torque behavior of the component through the gait cycle to provide support for specific musculoskeletal deficits. Certain existing devices permit adjusting such parameters. However, the ability to adjust each parameter independently of the others is desirable for ease of use and avoidance of inadvertent miscalibration.

A need therefore exists for an orthotic ankle joint device providing independently adjustable resistances to plantarflexion and dorsiflexion, equilibrium ankle alignment angle, and maximum limits on dorsiflexion and plantarflexion movements from the equilibrium ankle alignment angle. In addition, in existing orthotic ankle joint devices, it can be difficult if not impossible to set dorsiflexion resistances that are stiff enough to stabilize the wearer's ankle and knee against hyperflexion while at the same time soft enough to permit natural movement of the joint in a wearer's walking gait. An orthotic ankle joint device to address this challenge is also needed.

SUMMARY OF THE INVENTION

According to an aspect of the invention, a triple-action ankle joint device is provided. The device comprises a joint body, an attachment member (which may, for example, be a splint member or a socket for receiving a splint member) pivotally connected to the joint body for opposite dorsiflexion and plantarflexion movements (defined as movements produced by dorsiflexion and plantarflexion of a wearer's foot), a plantarflexion resistance spring, an initial dorsiflexion resistance spring, and a terminal stance dorsiflexion resistance spring.

The plantarflexion resistance spring is configured to bias the attachment member in a dorsiflexion direction relative to the joint body when the attachment member is within a plantarflexion resistance spring active angular range. The plantarflexion resistance spring active angular range begins at a plantarflexion resistance spring recruitment angle and increases in plantarflexion angle therefrom.

Likewise, the initial dorsiflexion resistance spring is configured to bias the attachment member in a plantarflexion direction relative to the joint body when the attachment member is within an initial dorsiflexion resistance spring active angular range, the initial dorsiflexion resistance spring active angular range beginning at an initial dorsiflexion resistance spring recruitment angle and increasing in dorsiflexion angle therefrom.

Additionally, the terminal stance dorsiflexion resistance spring is configured to bias the attachment member in a plantarflexion direction relative to the joint body when the attachment member is within a terminal stance dorsiflexion resistance spring active angular range; the terminal stance dorsiflexion resistance spring active angular range having at least a terminal stance dorsiflexion resistance spring recruitment angle and an angular range increasing in dorsiflexion therefrom. The terminal stance dorsiflexion resistance spring recruitment angle is greater in dorsiflexion than the initial dorsiflexion resistance spring recruitment angle, and typically operates at least in an angular range from the recruitment angle to the maximum dorsiflexion angle of the wearer's gait. In addition, the terminal stance dorsiflexion spring may operate at smaller dorsiflexion angles than its recruitment angle, but as the term "recruitment angle" is defined herein, the initial dorsiflexion resistance spring dominates the torque response of the attachment member between its recruitment angle and that of the terminal stance dorsiflexion resistance spring.

In one embodiment, the initial dorsiflexion resistance spring and the terminal stance dorsiflexion resistance spring are comprised in a single spring. The single spring is in effect a compound or staged spring, having a higher effective spring rate in the terminal stance dorsiflexion resistance spring active angular range than in a range of angles between the initial dorsiflexion resistance spring recruitment angle and the terminal stance dorsiflexion resistance spring recruitment angle. The single spring may be composed of discrete, separate structural sections that produce the respective higher and lower spring rates. Alternatively, for example, the spring may be a uniform mass of material that exhibits non-linear or staged resistance to compression, or it may have evenly distributed gaps or voids along its length, which are diminished in in initial lower spring rate phase or mode of spring deflection, and when the gaps or voids are fully closed, the spring may operate in a higher spring rate phase or mode of spring deflection.

Preferably, the attachment member is positionable in at least one neutral angle relative to the joint body in which a net biasing torque transmitted to the attachment member from the joint body is zero. The neutral angle is an angle between the angle of greatest plantarflexion in the plantarflexion resistance spring active angular range and the angle of greatest dorsiflexion in the initial dorsiflexion resistance spring active angular range, such that the attachment member is biased toward the neutral position when a wearer's foot is plantarflexed to the limit of the mechanism or dorsiflexed to the end of a second rocker phase defined by the mechanism. More preferably, the plantarflexion resistance spring active angular range and the initial dorsiflexion resistance spring active angular range do not even partially overlap, but rather only meet at the neutral angle, the neutral angle thus being equal to the angle of least plantarflexion in the plantarflexion resistance spring active angular range and to the angle of least dorsiflexion in the initial dorsiflexion resistance spring active angular range. In this manner, no biasing torque is transmitted to the attachment member at the neutral angle from any of the plantarflexion resistance spring, the initial dorsiflexion resistance spring, and the terminal stance dorsiflexion resistance spring, to facilitate independent substitution of any of those springs, independent adjustment of any of their pre-loads or spring rates, and independent adjustment of any of their active ranges of motion.

Independent adjustment of these torque response and range of motion parameters is achieved, for example, by appropriately sized, shaped, and positioned dorsiflexion resistance and plantarflexion resistance transmission members. In particular, a dorsiflexion transmission member may be operatively connected between the joint body and the attachment member and biased to move toward the attachment member in a direction that opposes dorsiflexion movement of a dorsiflexion-resist contact surface of the attachment member, a fixed dorsiflexion-resist stop restricting the dorsiflexion opposing movement toward the attachment member beyond a neutral position of the dorsiflexion-resist transmission member where the dorsiflexion-resist transmission member abuts the dorsiflexion-resist contact surface of the attachment member disposed at the neutral angle.

Likewise, a plantarflexion-resist transmission member may be operatively connected between the joint body and the attachment member and biased to move toward the attachment member in a direction that opposes plantarflexion movement of a plantarflexion-resist contact surface of the attachment member, a fixed plantarflexion-resist stop restricting the dorsiflexion opposing movement toward the attachment member beyond a neutral position of the plantarflexion-resist transmission member where the plantarflexion-resist transmission member abuts the plantarflexion-resist contact surface of the attachment member disposed at the neutral angle.

For example, the transmission members may be cam follower pins or ball bearings disposed between a spring and a cam surface of the attachment member, whose excursion from respective channels in the joint body in which they are housed is limited by appropriate stop members.

Alternatively, they may simply be the free ends of respective springs affixed to the joint body at opposite ends, in which case the extent of their motion is limited to the position at which the respective spring (or a portion of it comprising the free end) is fully relaxed, and they will not push a cam surface of the attachment member beyond such a point.

In other variations, the initial dorsiflexion resistance spring and terminal stance dorsiflexion resistance spring may be arranged in parallel or in series between the ankle joint body and the attachment member. Further, springs in a parallel arrangement may be positioned as desired, such as concentrically or side-by-side, a side-by-side arrangement advantageously providing the possibility of amplifying the resistance force provided by the terminal stance dorsiflexion resistance spring by employing it to apply a force to the attachment member farther from its pivotal axis. On the other hand, a functionally equivalent concentric parallel arrangement may be more compact in some dimensions than a side-by-side parallel arrangement.

In a parallel arrangement of the dorsiflexion resistance springs, an initial dorsiflexion resisting force may be transmitted from the ankle joint body to the attachment member by a load path avoiding the terminal stance dorsiflexion resistance spring, the terminal stance dorsiflexion resistance spring only beginning to deflect at its recruitment angle, at which point the terminal stance dorsiflexion resistance spring dominates the overall behavior of the parallel arrangement.

In a series arrangement of the dorsiflexion resistance springs, the initial load path may pass through the terminal stance dorsiflexion resistance spring, but the springs are arranged so that they are permitted to deflect by different amounts to transmit an equal force. Thus, if one of the springs has a much lower spring rate/spring constant, as the initial dorsiflexion resistance spring typically does, that spring will dominate the overall behavior of the series arrangement. At the recruitment angle of the terminal stance dorsiflexion resistance spring, the arrangement may transition to parallel, or further deflection of the initial dorsiflexion resistance spring may be halted altogether such that the terminal stance dorsiflexion resistance spring bears essentially all additional dorsiflexion resistance loading.

Recruitment of the terminal stance dorsiflexion resistance spring may be effected by the engagement of an essentially rigid initial range of dorsiflexion limiting member at the terminal stance dorsiflexion resistance spring recruitment angle. This limiting member may, for example, stand in parallel with the initial dorsiflexion resistance spring to isolate the latter from any further deflection, to transmit essentially all of a terminal dorsiflexion resisting force from the terminal stance dorsiflexion resistance spring to the attachment member by a load path avoiding the initial dorsiflexion resistance spring, and to convert essentially all further dorsiflexion movement of the attachment member to deflection of the terminal stance dorsiflexion resistance spring.

The limiting member may initially be spaced by a clearance from a terminal stance dorsiflexion resistance spring engagement surface (e.g., a surface of the spring itself or of a rigid member disposed against an end of the spring) when the attachment member is at the initial dorsiflexion resistance spring recruitment angle. In some embodiments, this clearance is adjustable without affecting a preload (i.e., a load at the neutral angle and/or at a recruitment angle) of either dorsiflexion resistance spring, and in other embodiments, adjusting this clearance changes a preload of one or both springs.

Dorsiflexion movement of the attachment member from the initial dorsiflexion resistance spring recruitment angle to the terminal stance dorsiflexion resistance spring recruitment angle impels movement of the initial range of dorsiflexion limiting member against the terminal stance dorsiflexion resistance spring engagement surface, which in turn impels movement of the terminal stance dorsiflexion resistance spring engagement surface when the attachment member continues to move in dorsiflexion, which in turn produces the terminal stance dorsiflexion resistance force. The terminal stance force increases with dorsiflexion angle at a higher rate than the initial force, which may be effected by greater stiffness of the terminal stance spring and/or a mechanical advantage afforded to the terminal stance spring, such as by positioning it farther from a pivotal axis of the attachment member relative to the joint body than the initial dorsiflexion resistance spring.

In one embodiment, the initial dorsiflexion resistance spring is a helical spring disposed to be loaded in compression by dorsiflexion movement beyond the initial dorsiflexion resistance spring recruitment angle, and the initial range of dorsiflexion limiting member is an elongate rod disposed in an interior channel extending through the initial dorsiflexion resistance spring.

In another embodiment, the terminal stance dorsiflexion resistance spring engagement surface is maintained in a fixed position relative to an attachment member engaging end of the terminal stance dorsiflexion resistance spring, a position of the terminal stance dorsiflexion resistance spring engagement surface being adjustable by adjusting a position of a joint body engaging end of the terminal stance dorsiflexion resistance spring relative to the joint body.

In another embodiment, a first initial range of dorsiflexion limiting member is spaced by a first clearance from a first terminal stance dorsiflexion resistance spring engagement surface when the attachment member is at the initial dorsiflexion resistance spring recruitment angle, the terminal stance dorsiflexion resistance spring being deflectable to produce said terminal dorsiflexion resisting force by movement of said first terminal stance dorsiflexion resistance spring engagement surface, and a first terminal stance dorsiflexion resistance spring engagement surface is fixed relative to an attachment member engaging end of the terminal stance dorsiflexion resistance spring.

Additionally, a second initial range of dorsiflexion limiting member is spaced by a second clearance from a second terminal stance dorsiflexion resistance spring engagement surface when the attachment member is at the initial dorsiflexion resistance spring recruitment angle, the terminal stance dorsiflexion resistance spring being deflectable to produce said terminal dorsiflexion resisting force by movement of said second terminal stance dorsiflexion resistance spring engagement surface. A second terminal stance dorsiflexion resistance spring engagement surface is configured to maintain a fixed position relative to an attachment member engaging end of the terminal stance dorsiflexion resistance spring when subjected to a force in a direction of movement impelled by dorsiflexion movement of the attachment member, said fixed position of the second terminal stance dorsiflexion resistance spring engagement surface being adjustable relative to a position of a joint body engaging end of the terminal stance dorsiflexion resistance spring. The attachment member is configured to move the first initial range of dorsiflexion limiting member toward the first terminal stance dorsiflexion resistance spring engagement surface and the second initial range of dorsiflexion limiting member toward the second terminal stance dorsiflexion resistance spring engagement surface upon further dorsiflexion movement of the attachment member from the initial dorsiflexion resistance spring recruitment angle. In this case, the terminal stance dorsiflexion resistance spring recruitment angle being an angle of the attachment member at which one of the first initial range of dorsiflexion limiting member and the second initial range of dorsiflexion limiting member contacts the respective first or second terminal stance dorsiflexion resistance spring engagement surface.

The attachment member may comprise a stirrup head having a dorsiflexion cam surface and a plantarflexion cam surface to convert its pivotal movement into deflections of the dorsiflexion resistance and plantarflexion resistance springs, respectively. Operatively disposed between the respective cam surfaces and springs are a dorsiflexion cam follower member mounted for linear movement relative to the joint body and a plantarflexion cam follower member mounted for linear movement relative to the joint body.

The cam follower members may be of a pin type, presenting a generally flat surface for contact with the respective cam surface, a ball type, presenting a generally hemispherical surface for contact with the respective cam surface, or any other suitable type or shape.

Thus, the dorsiflexion cam surface, when in the active angular range of the initial dorsiflexion resistance spring or the terminal stance dorsiflexion resistance spring, engages the dorsiflexion follower member in normal contact so that dorsiflexion rotation of the dorsiflexion cam surface produces a loading translation of the dorsiflexion follower member, resulting in increased dorsiflexion resistance loading of at least one of the initial dorsiflexion resistance spring and the terminal stance dorsiflexion resistance spring.

Conversely, plantarflexion rotation of the dorsiflexion cam surface produces an unloading translation of the dorsiflexion follower pin, resulting in decreased dorsiflexion resistance loading of at least one of the initial dorsiflexion resistance spring and the terminal stance dorsiflexion resistance spring. Likewise, the plantarflexion cam surface, when in the active angular range of the plantarflexion resistance spring, engages the plantarflexion follower member in normal contact so that plantarflexion rotation of the plantarflexion cam surface produces a loading translation of the plantarflexion follower member and increased loading of the plantarflexion resistance spring, and dorsiflexion rotation of the plantarflexion cam surface produces an unloading translation of the plantarflexion follower member and unloading of the plantarflexion resistance spring.

In accordance with another aspect of the invention, an ankle joint device having an independently adjustable neutral angle is provided. The device may comprise essentially all of the components of the triple action device described above, or it may omit, for example, the terminal stance dorsiflexion resistance spring. In addition, the device comprises a second attachment member pivotally connected to the joint body and extending from the joint body in a direction generally opposite to that in which the first attachment member extends. The device further includes a locking mechanism operable to lock the second attachment member at a selected angle relative to the joint body. One of the attachment members attaches to a wearer's foot, and the other to the corresponding lower leg. Thus, the neutral angle may be adjusted independently of plantarflexion and dorsiflexion ranges of motion and resistance torque preloads and responses. Changing the neutral angle also displaces the absolute extremes of plantarflexion and dorsiflexion of the wearer's foot relative to the wearer's lower leg permitted by the mechanism, as the plantarflexion and dorsiflexion ranges of motion of the device are set relative to the neutral angle.

In accordance with another aspect of the invention, an orthosis is provided including the components of the triple action ankle joint as described above, and further comprising a second attachment member, so that one of the two attachment members can attach to a wearer's leg, and the other to the wearer's foot. In this aspect of the invention, a neutral angle of the second attachment member relative to the lower attachment member may or may not be adjustable.

In accordance with another aspect of the invention, a method of making an ankle joint device is provided. The method comprises forming an assembly of a joint body, an attachment member, a plantarflexion resistance spring, an initial dorsiflexion resistance spring, and a terminal stance dorsiflexion resistance spring, and assembling those components substantially to produce the structure and function described above for the triple action joint.

In accordance with another aspect of the invention, a method of supporting an ankle of a human in a range of dorsiflexion and plantarflexion motions is provided. The method uses a triple action joint device, substantially as described above, and further comprises attaching the attachment member to one of a foot and a lower leg corresponding to said ankle; and attaching the joint body to the other of the foot and the lower leg, the attached attachment member being configured to move in said dorsiflexion direction relative to the attached joint body when the human's foot dorsiflexes and in said plantarflexion direction relative to the attached joint body when the human's foot plantarflexes.

DETAILED DESCRIPTION OF THE INVENTION

Orthotic ankle joint devices and therapeutic and adaptive methods of treating lower limb biomechanical deficits according to the invention will now be described, with reference to features and embodiments illustrated in the accompanying drawings.

The illustrated devices and methods provide plantarflexion ("PF") resistance by way of a PF-resist spring producing a force that limits foot slap in the wearer, but which is not so stiff as to cause the wearer to excessively flex the knee—to compensate for reduced plantarflexion—in rotating the foot forward to bring the ball of the foot into contact with the ground after heel strike. Dorsiflexion ("DF") resistance is likewise provided by a DF-resist spring. In the illustrated embodiments, the PF-resist and DF-resist springs are linear compression springs. However, the invention is not limited to devices using springs that deflect rectilinearly or in compression, or for that matter to solid state springs. A more general discussion of resistive elements within the scope of the invention is included later.

The illustrated devices and methods provide a step up in mid- to late-stance dorsiflexion resistance, to improve stance control in a wearer with a knee extensor insufficiency. The relationship between dorsiflexion and a knee extension is as follows: When the foot is planted, dorsiflexion of the foot entails pivoting the lower leg forward. In response, the knee tends to flex to keep the body's center of mass over the planted foot. Thus, the more the foot dorsiflexes in late stance, the more the knee must flex to maintain stability. In turn, the more the knee flexes, the harder the knee extensor has to work to support one's weight. Accordingly, limiting maximum dorsiflexion can reduce the heaviest torque loads on a knee extensor. Likewise, sudden onset of heavy knee extensor loading can be prevented by slowing the rate of ankle dorsiflexion in late stance. Thus, according to the present invention, a wearer's actual maximum dorsiflexion and/or the rate at which that maximum dorsiflexion is approached are limited by increasing the resistance to dorsiflexion as the dorsiflexion angle approaches the angle of maximum dorsiflexion, corresponding to a "terminal stance" state or position of the wearer's gait. The increase in resistance is preferably an abrupt stepwise increase, occurring at a desired dorsiflexion angle near the dorsiflexion angle corresponding to terminal stance.

Figures 1A, 1B:
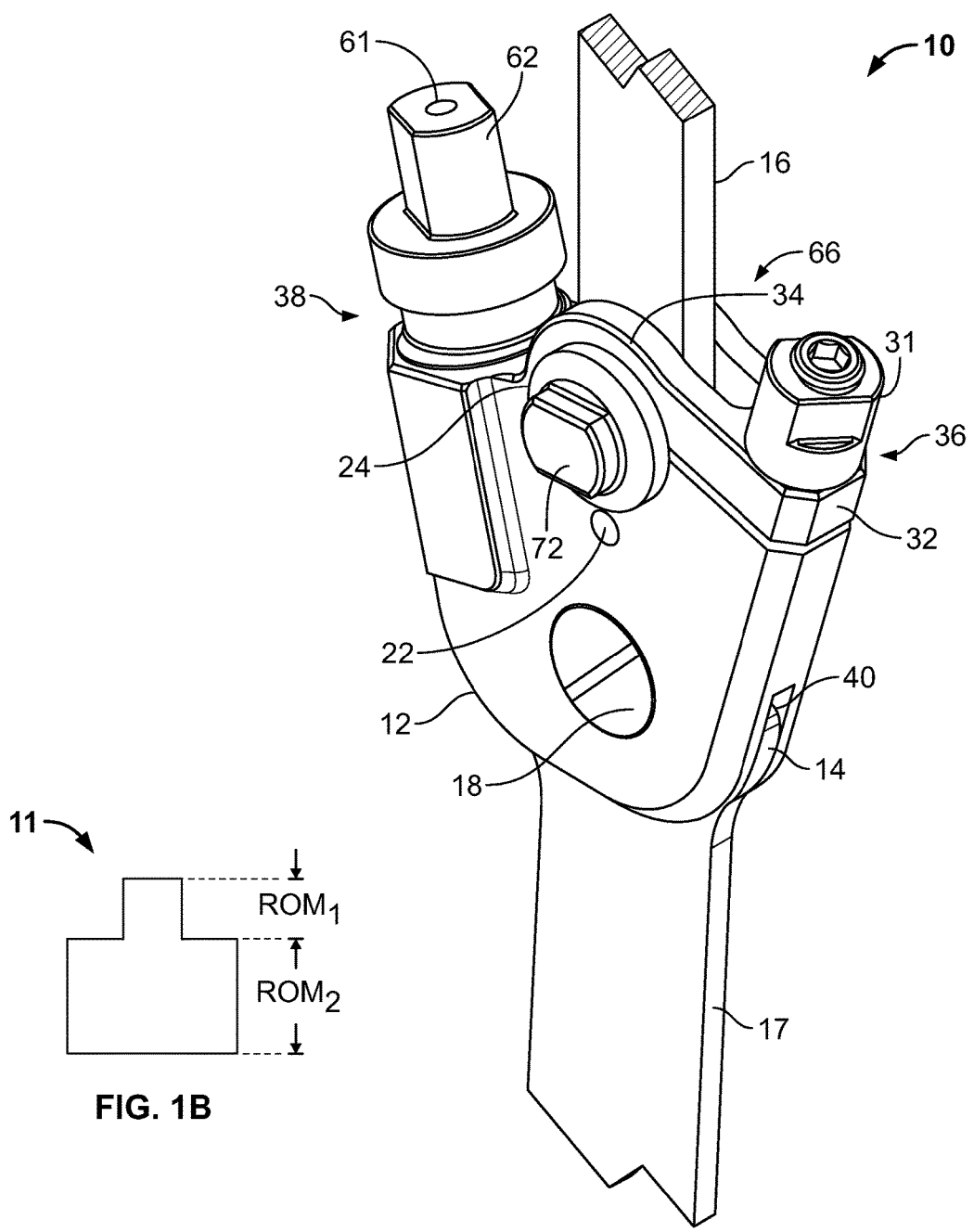
FIG. 1A is a perspective view of an ankle joint device according to an embodiment of the invention.
FIG. 1B is a schematic representation of a staged or compound dorsiflexion resistance spring for use in an ankle joint device according to an aspect of the invention.

The stepwise increase in resistance may be produced by "recruiting" a second, stiffer terminal stance DF-resist spring at a terminal stance spring recruitment angle, as in the illustrated embodiments. Alternatively, an initial (or "second rocker") DF-resist spring and a terminal stance DF-resist spring may be the same spring, such as a compound or staged DF-resist spring 11, represented schematically in FIG. 1B. Spring 11 exhibits a lower first spring rate over an initial range of deflection $ROM_1$ and abruptly transitioning to a higher second spring rate over a subsequent range of deflection $ROM_2$. The transition in spring rates is depicted schematically as a width increase, but spring 11 is not necessarily physically wider over some stiffer portion of its length. Instead, for example, it may be a coil spring that transitions to a heavier gauge or stiffer material at some point, two blocks of different compressible materials of different compression rates joined together, or some other combination of two joined sections of approximately the same width, the step up in resistance being provided by one of the sections being compressed to an effective maximum limit, such as in a coil spring compressed until the gaps between successive coils close. Alternatively, the structure of spring 11 may be essentially uniform along its entire length, the step up in resistance (such as a spring rate, which is expressed in force/distance units such as lbf/in) being provided by the entire spring being compressed to the limit of one mode of compression and another mode begins to dominate the behavior of the spring, such as when longitudinal gaps or voids are closed, and solid material begins to deform by compressing longitudinally and expanding transversely, for example. Regardless of whether a single compound or staged spring or two separate DF-resist springs is/are employed as the initial and terminal stance springs, the term "recruitment angle" will be understood to refer to an angle at which a spring or a mode of deformation or deflection becomes the dominant spring or dominant mode. For example, an angle at which a stiffer (higher spring rate) spring/mode and a softer (lower spring rate) spring/mode are simultaneously engaged in series, or only the softer spring/mode is engaged, is referred to herein as the recruitment angle of the softer spring. On the other hand, an angle at which the two springs/modes are engaged in parallel, or only the stiffer spring/mode is engaged, is referred to as the recruitment angle of the stiffer spring/mode. Thus, in the case of a compound or staged spring 11 serving as both the initial DF-resist spring and the terminal stance DF-resist spring, the "initial DF-resist spring recruitment angle" refers to the angle at which spring 11 begins to be compressed, and the "terminal stance spring recruitment angle" refers to the angle at which the softer mode of deflection essentially ceases to operate and the stiffer mode of deflection abruptly becomes dominant.

In addition to providing resistance to plantarflexion over an active plantarflexion range and two distinct phases of resistance over an active dorsiflexion range, devices according to the invention permit several parameters to be adjusted independently. These include dorsiflexion and plantarflexion resistance preloads, range of permitted dorsiflexion motion from sagittal alignment, range of permitted plantarflexion motion from sagittal alignment, and the angle in the sagittal plane between a lower leg attachment member (such as a lower leg splint, also termed a "tibial shank", or a socket or other structure into which a lower leg splint/tibial shank may be inserted, and which will move together with the lower leg splint/tibial shank) and a foot attachment member (one or the other of the attachment members, typically the foot attachment member, typically comprising a stirrup component) at a neutral position of the foot attachment member from which it is not biased in either direction.

As the lower leg attachment member is affixed to the wearer's lower leg and the foot attachment member is affixed to the wearer's foot, the angle between the splint mounting and stirrup defines a neutral or equilibrium ankle alignment angle between the wearer's lower leg and foot, in the sagittal plane. In the embodiments described below, this angle is referred to as a "tibial shank angle," with reference to the structure of the device. The neutral sagittal tibial shank angle will be understood to be the same angle as the "(equilibrium/neutral) ankle alignment angle" or simply "alignment angle" of the device. The neutral sagittal tibial shank angle is the angle by which the upper bar is displaced from its vertical orientation when the foot attachment member is in a neutral position and the wearer's foot is horizontal (planted). To facilitate measuring and adjusting the neutral sagittal tibial shank angle, the vertical orientation of the upper bar may be marked by a vertical line or notch on the joint body, provided that, as in the illustrated embodiments, the orientation of the joint body relative to the neutral position of the foot attachment member does not change with any adjustments to the device.

The scope of the invention is not limited to devices in which the reference structure affixed to a wearer's lower leg is a bar or shank. Likewise, any suitable leg retention structure may be secured directly to a wearer's lower leg and connected to the lower leg attachment member. Ankle joint devices according to the invention are suitable for use in any orthosis comprised of body mounted segments that exert control across the ankle joint, including, but not limited to, ankle-foot orthoses ("AFOs"), knee-ankle-foot orthoses ("KAFOs"), and hip-knee-ankle-foot orthoses ("HKAFOs"), typically fabricated using metal and other materials including, but not limited to, leather, polymer, filled polymer, and composite materials. In addition, though not shown in any illustrated embodiment, the device may alternatively be inverted so that the upper/leg attachment member is the member that pivots under resistance torque loads relative to the joint body with flexion of a wearer's foot, while the lower/foot attachment member is the member that is adjustably locked at a selected angle relative to the joint body.

First Illustrated Embodiment

A first illustrated embodiment of an orthotic ankle joint device according to the invention is shown as ankle joint device 10 in FIGS. 1-10B, and an alternative embodiment is shown as ankle joint device 74 in FIGS. 11-19. Referring to the perspective and side elevation drawings of FIGS. 1-3, ankle joint device 10 includes a joint body 12 pivotally connected to a normal contact stirrup 14 and to an upper bar 16 that may serve as a lower leg splint mounting bar or tibial shank. Stirrup 14, typically formed in the upper end of a lower bar 17 which may be attached to a foot orthotic or other similar structure constraining it to pivot in tandem with plantarflexion and dorsiflexion of the wearer's foot, is pivotally mounted to joint body 12 by a stirrup bushing screw 18 connected to a stirrup bushing 20, shown in FIG. 3. Similarly, upper bar 16 is pivotally mounted to an upper bar pivot pin 22. For convenience, the terms "active/relative PF/DF ROM" or "active/relative PF/DF angle" are used herein to mean an angular range of motion or angle of a foot attached component (such as stirrup 14) relative to a sagittal neutral alignment angle in a PF or DF direction. In addition, "absolute PF/DF ROM" and "absolute PF/DF angle" are used to refer to an angular range of motion or angle of stirrup 14 relative to upper bar 16—typically affixed to a wearer's leg and thus providing an absolute reference to its angular position—in a PF or DF direction. Additionally, a "second rocker ROM" refers to a range of motion in dorsiflexion from the sagittal neutral alignment angle to a recruitment angle of a terminal stance spring, which generally provides a step up in torque response to further dorsiflexion movement from the terminal stance spring recruitment angle. "Second rocker ROM" is not to be confused with an entire range of dorsiflexion motion permitted by the device. Indeed, a "hard stop" to dorsiflexion, such as may be formed of a solid piece of stainless steel or other generally incompressible material, is not typically necessary according to the invention, as the terminal stance spring is designed to provide a very stiff torque response, typically capable of resisting dorsiflexion torques of the magnitude produced by a wearer's gait when approaching terminal stance, without fully compressing the terminal stance spring. Thus, an entire active DF ROM could vary noticeably from wearer to wearer depending on the amount of dorsiflexion torque applied by the wearer in the third rocker/terminal stance phase.

A tibial shank angle adjustment cam 24 mated to a tibial shank angle adjustment cam bushing 26 is mounted in joint body 12 for rotation relative to joint body 12 when upper bar 16 is rotated relative to joint body 12 within a permitted adjustable range of tibial shank angles. An upper bar pocket cap 27 serves as a bushing for upper bar pivot pin 22 and as a seat for tibial shank angle adjustment cam bushing 26. Optionally, a visual tibial shank angle indicator feature 28 of tibial shank angle adjustment cam 24 cooperates with a scale 30 of joint body 12 to indicate a current tibial shank angle. In addition, tibial shank angle adjustment cam 24 and bushing 26 serve to facilitate locking the angular position of upper bar 16 by tightening a tibial shank angle locking bolt 31 to apply a clamping force to a clamping arm 32 of a tibial shank angle locking collar 34. This arrangement illustrates one way in which an angle of upper bar 16 relative to joint body 12 in the sagittal plane (a "sagittal alignment angle") may be adjusted and locked in place independently of the dorsiflexion and plantarflexion torque responses and independently of relative PF and DF ranges of motion (ROM). Advantageously, the tibial shank angle of joint device 10 can be adjusted to address (e.g., accommodate, treat/correct, or some combination) the particular condition of a wearer without a corresponding change in the support or assistance provided by joint device 10 at a given relative PF or DF angle.

Figure 7:
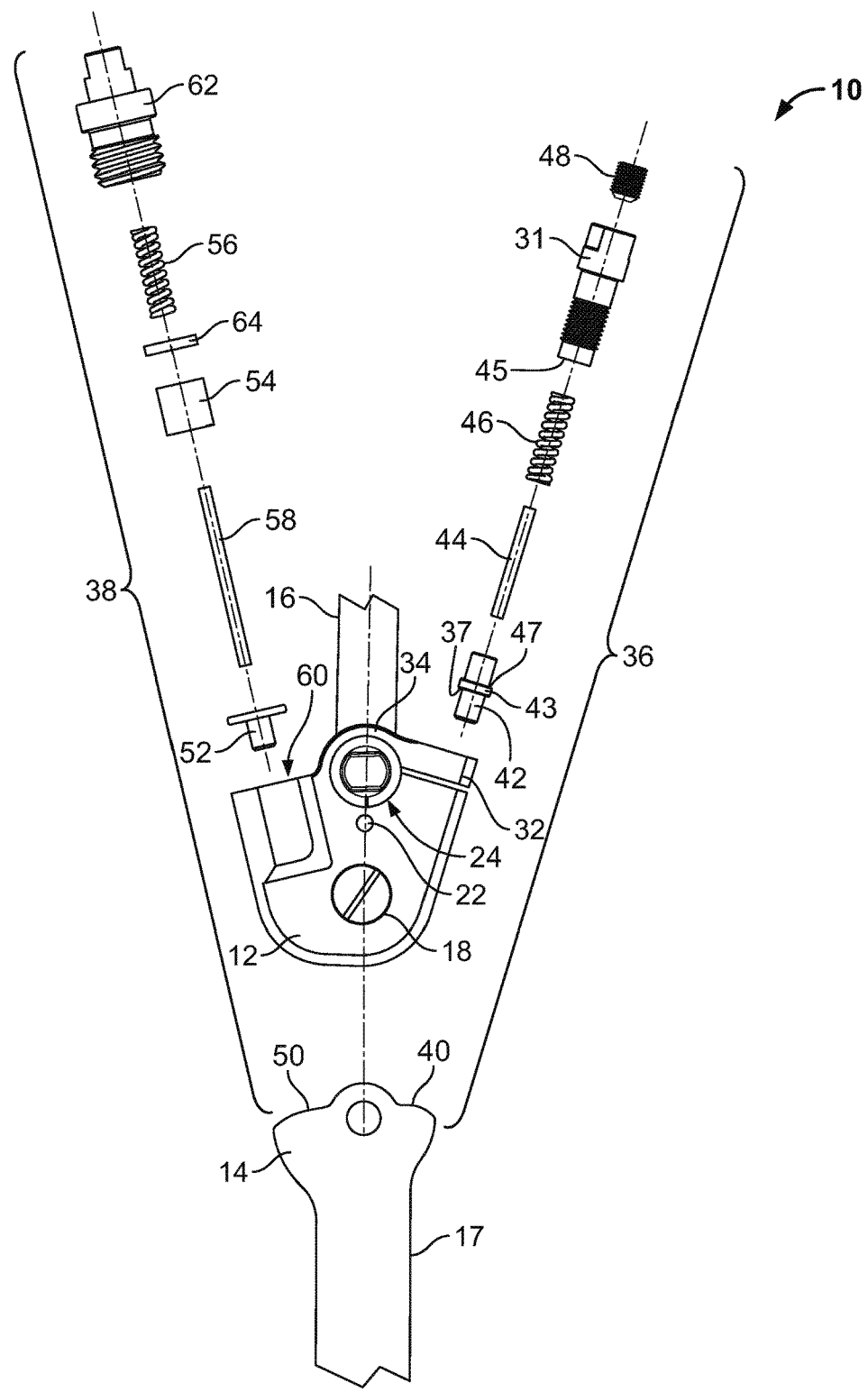
FIG. 7 is a left side exploded elevation view of the device shown in FIG. 1.
Figure 8:
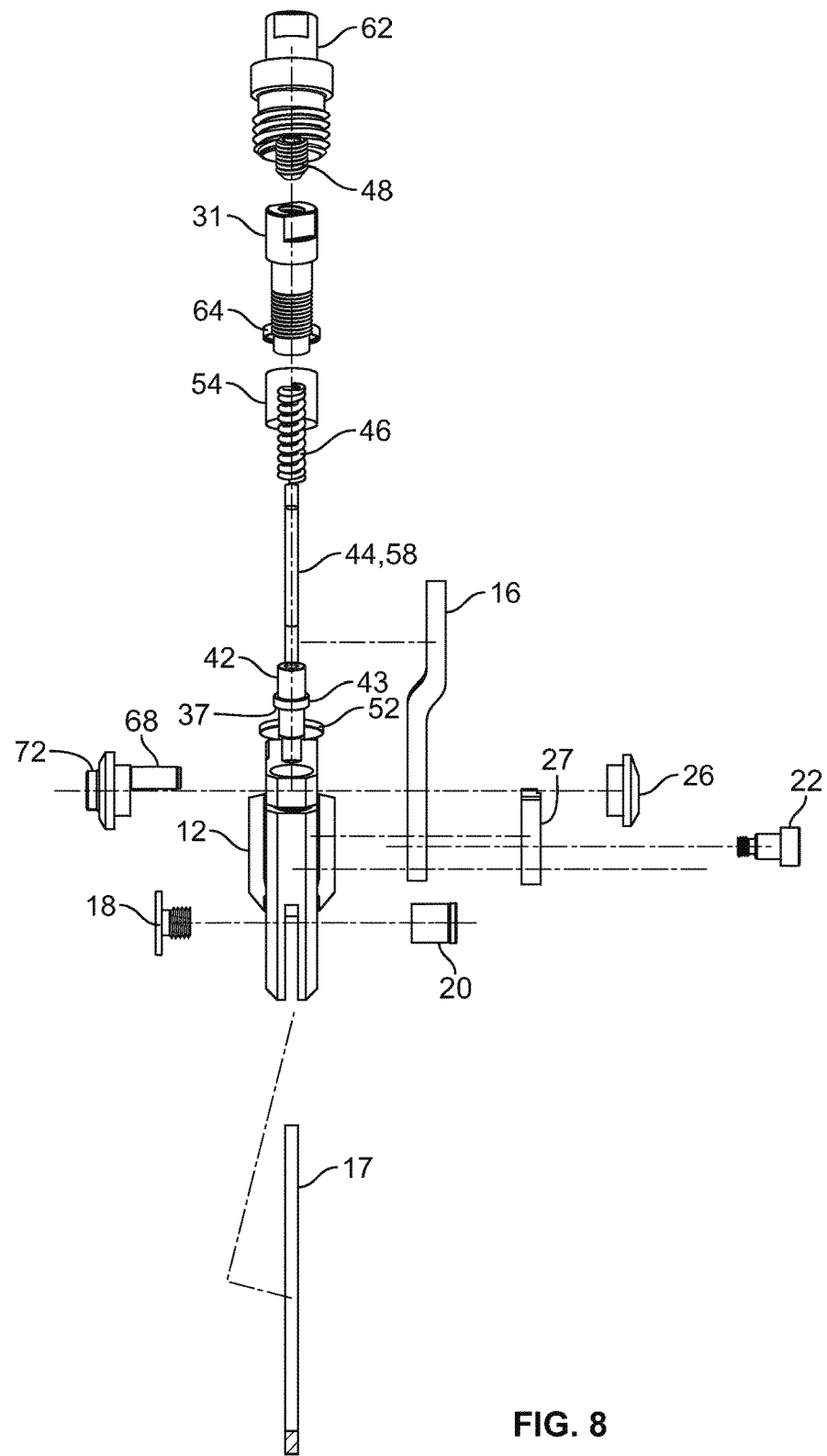
FIG. 8 is a rear exploded elevation view of the device shown in FIG. 1.
Figure 10A:
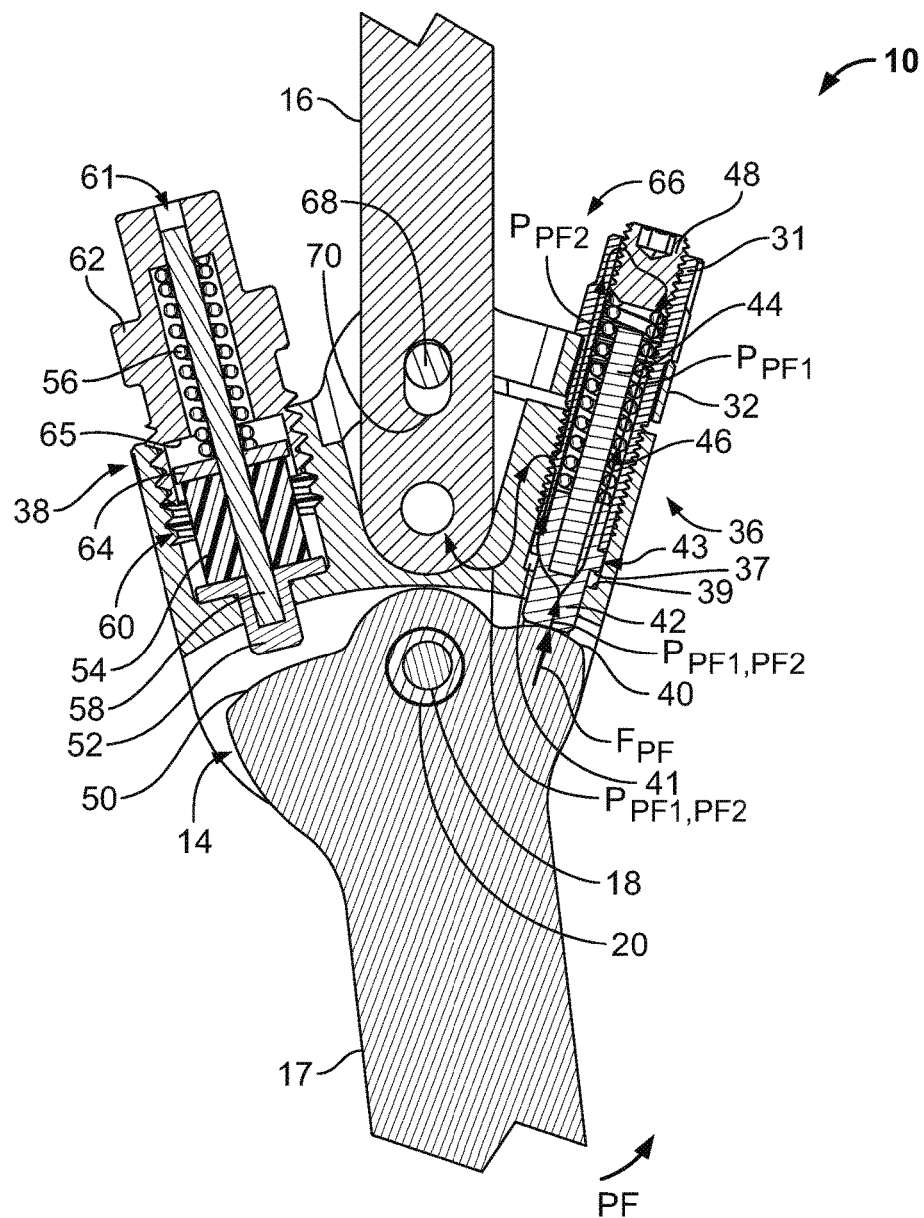
FIG. 10A is a left side sectional elevation view of the device shown in FIG. 1, depicting an orientation of the device within an active plantarflexion range of motion.

As best seen in the exploded view of FIG. 7 and the cross sectional elevation view of FIG. 10A, ankle joint device 10 includes a PF-resist assembly 36 and a DF-resist assembly 38. During use of joint device 10 as part of an AFO or KAFO, PF-resist assembly 36 provides resistance to plantarflexion of the wearer's foot (relative to a tibial shank angle) occurring in a "first rocker phase" of a human walking gait between heel strike and midstance, corresponding to the full range of plantarflexion motion. Similarly, DF-resist assembly 38 provides resistance to dorsiflexion in a "second rocker phase" (corresponding to a first range of dorsiflexion motion) of a human walking gait between midstance and terminal stance and a "third rocker phase"/"terminal stance phase" (corresponding to a second range of dorsiflexion motion) of a human walking gait in which the wearer's foot is maximally dorsiflexed, typically until just before the wearer's heel lifts from the ground.

Plantarflexion Resistance and Range of Motion

Figure 9:
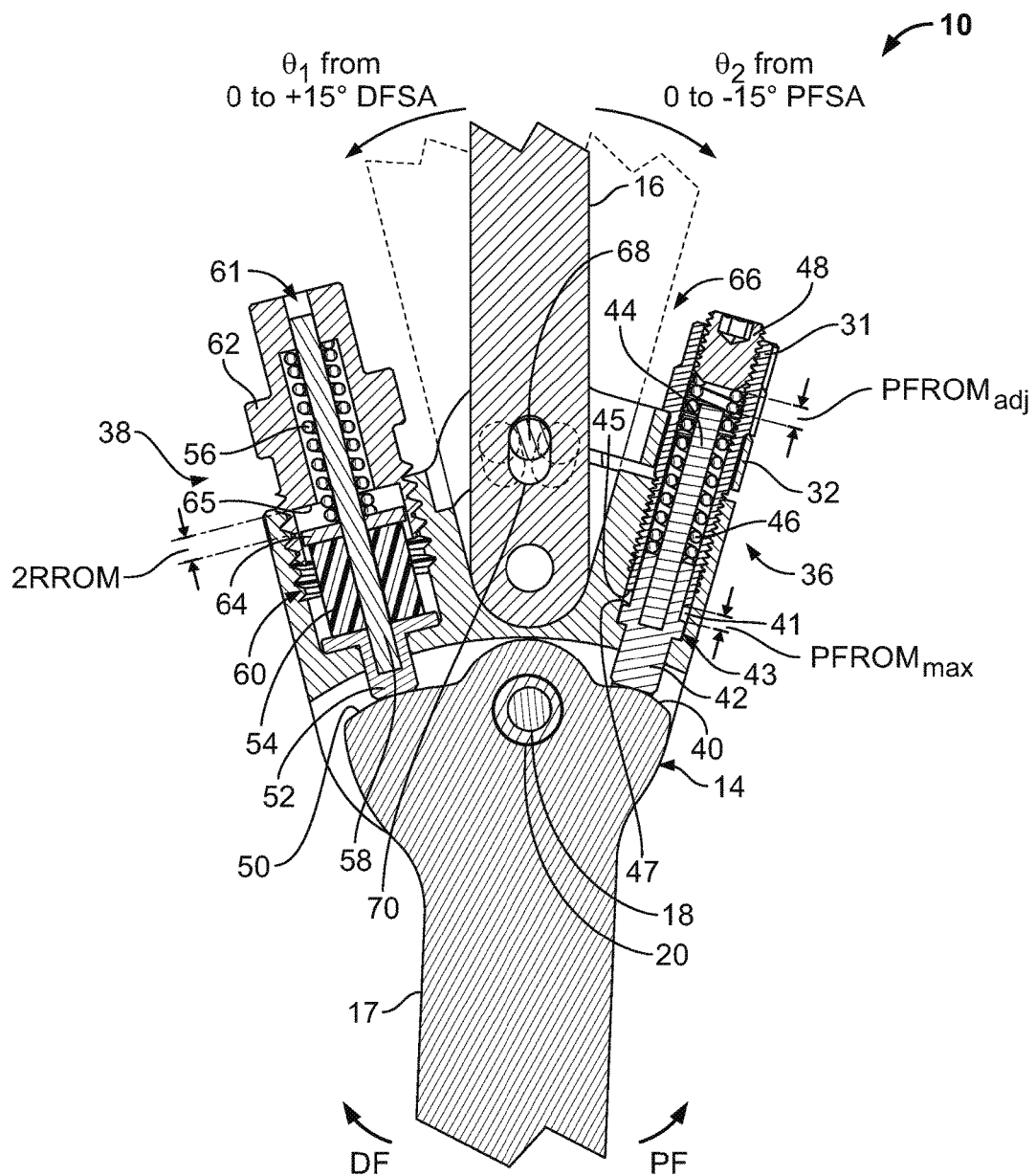
FIG. 9 is a left side sectional elevation view of the device shown in FIG. 1.
Figure 10B:
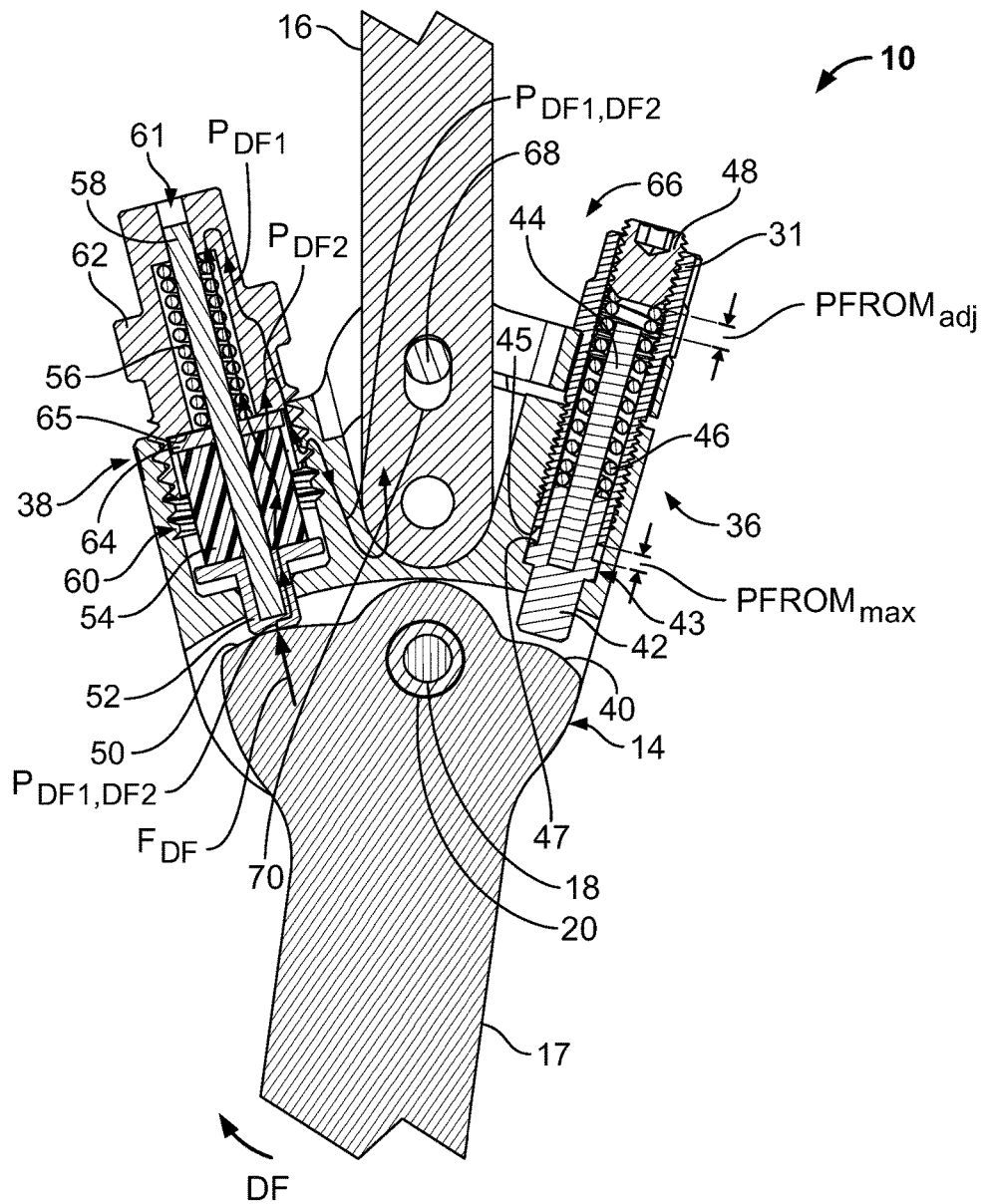
FIG. 10B is a left side sectional elevation view of the device shown in FIG. 1, depicting an orientation of the device at a terminal stance spring recruitment angle, at the end of a second rocker range of motion and within an overall dorsiflexion range of motion.
Figure 11:
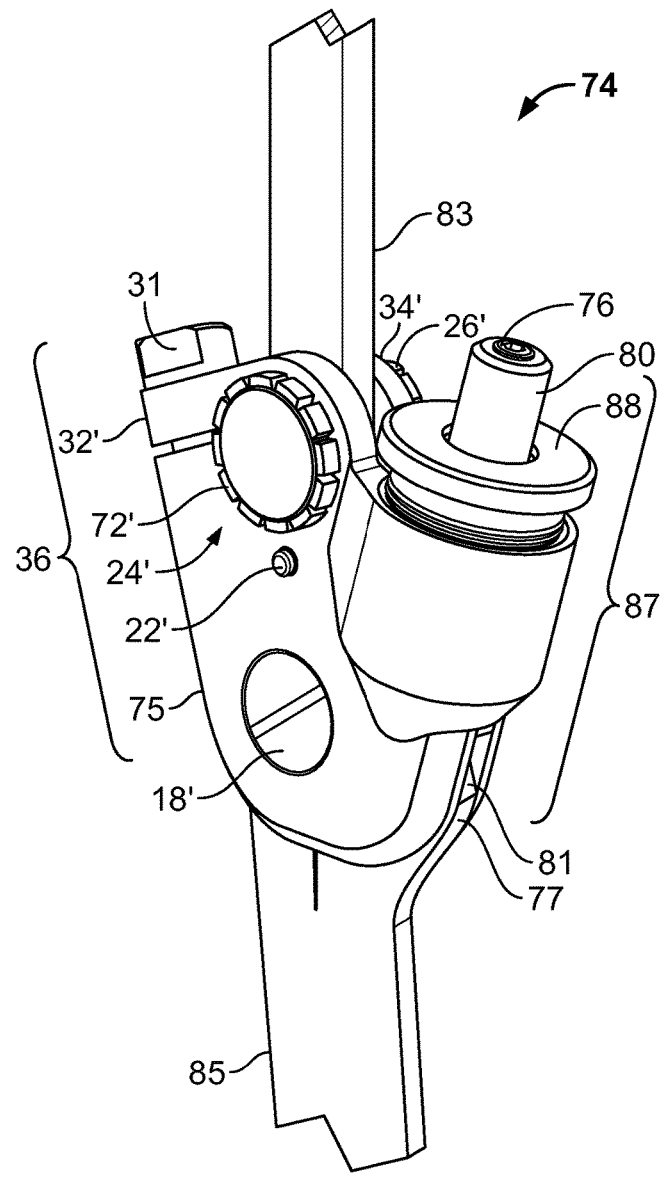
FIG. 11 is a perspective view of an ankle joint device according to another embodiment of the invention.
Figure 12:
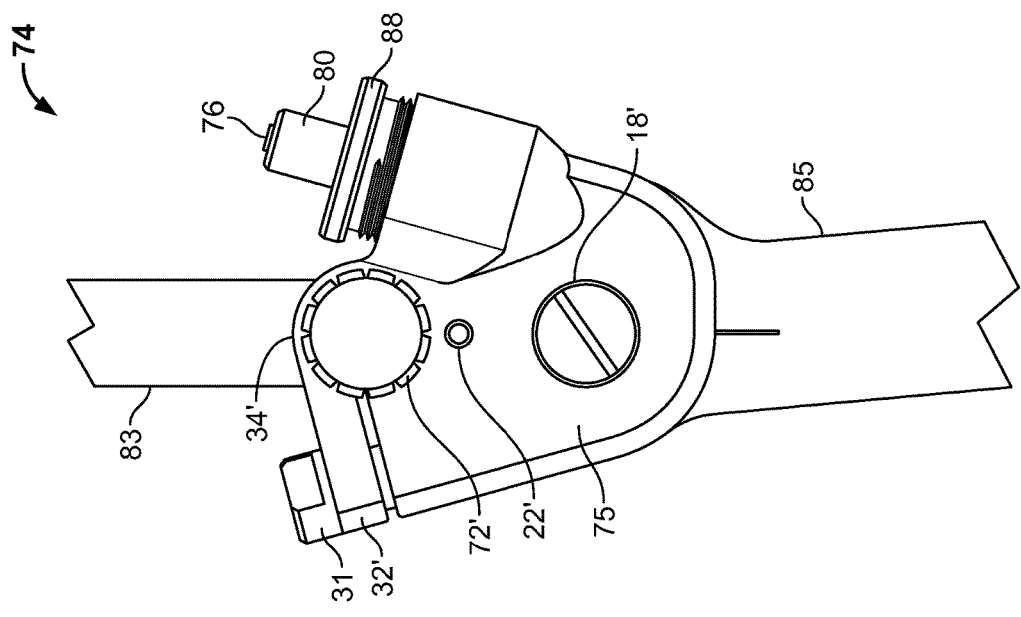
FIG. 12 is a left side elevation view of the device shown in FIG. 11.
Figure 13:
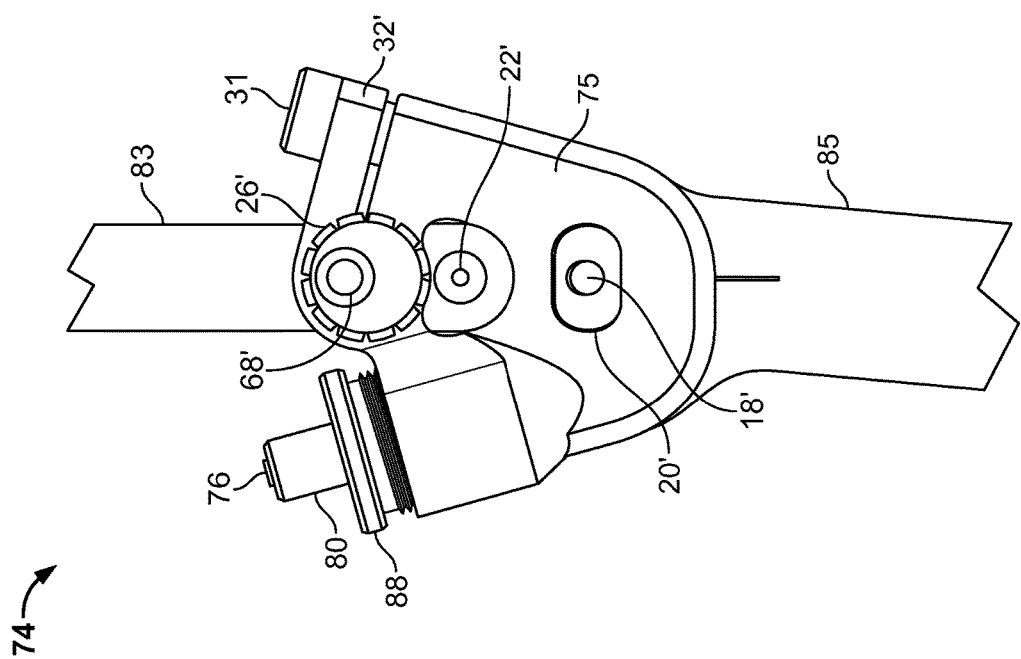
FIG. 13 is a right side elevation view of the device shown in FIG. 11.
Figure 15:
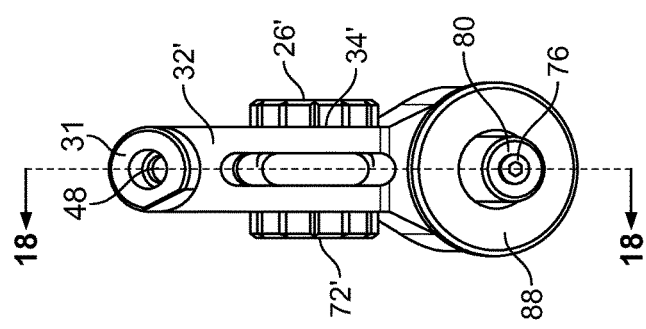
FIG. 15 is a top plan view of the device shown in FIG. 11.
Figure 14:
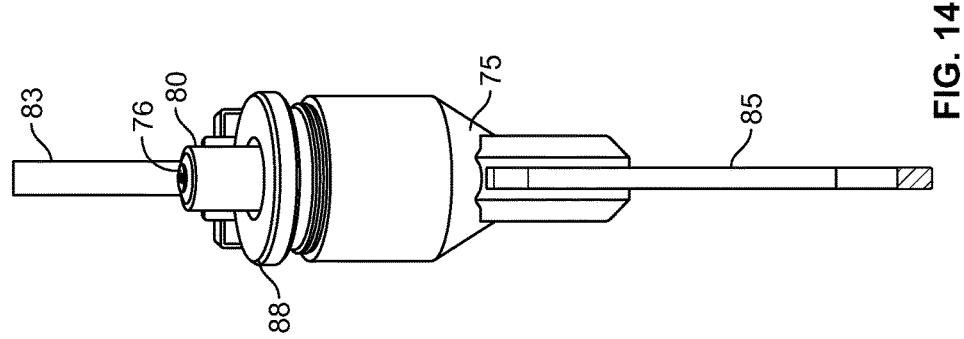
FIG. 14 is a front elevation view of the device shown in FIG. 11.
Figure 16:
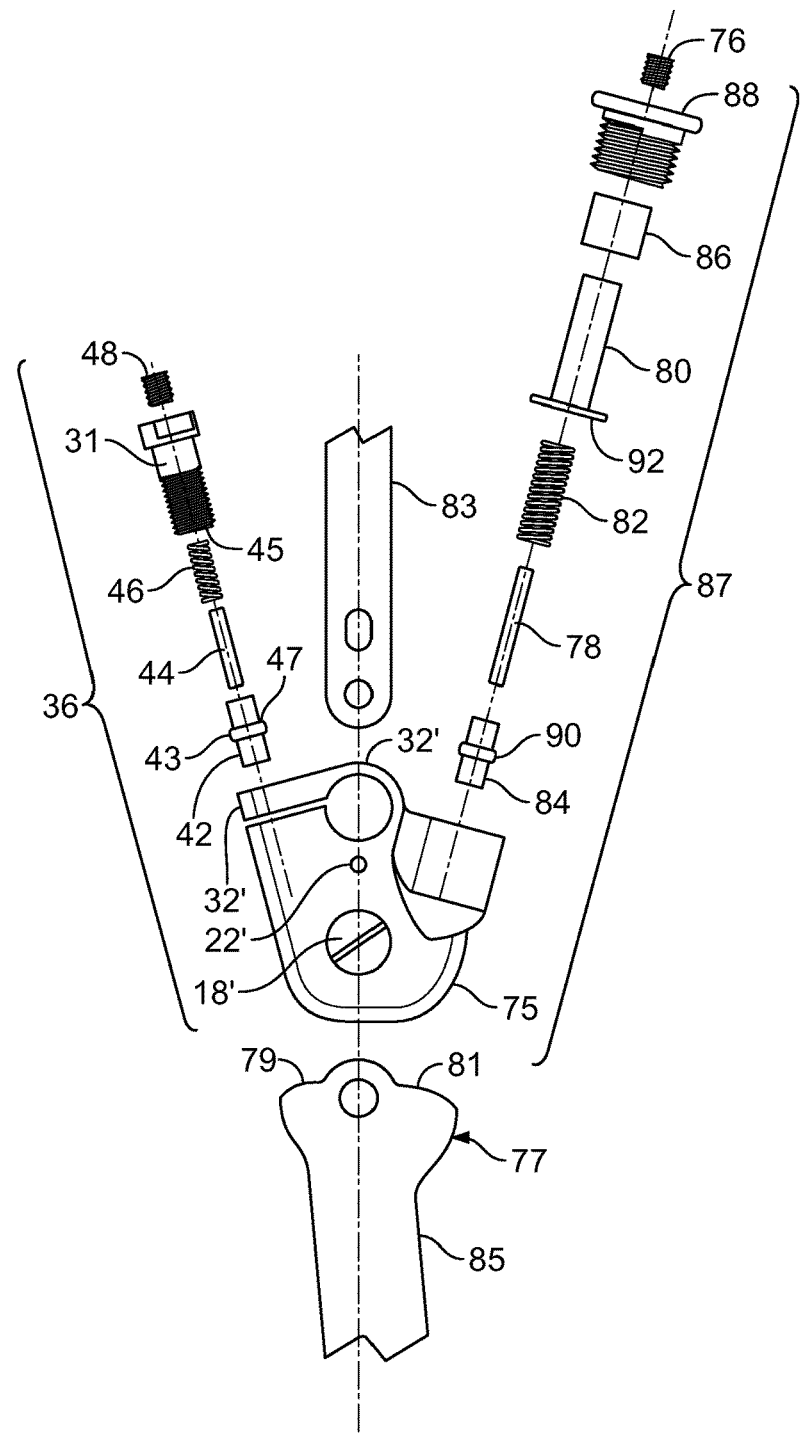
FIG. 16 is a right side exploded elevation view of the device shown in FIG. 11.
Figure 17:
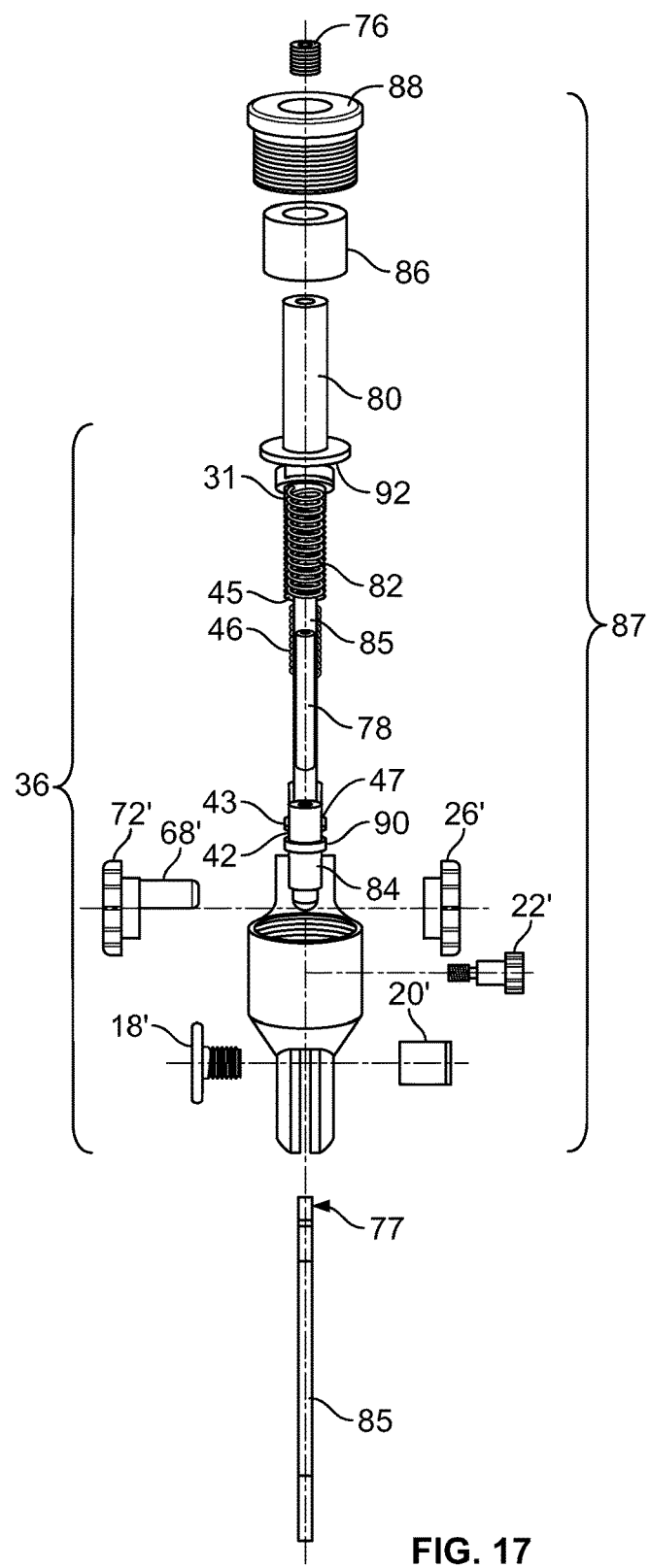
FIG. 17 is a front exploded elevation view of the device shown in FIG. 11.

PF-resist assembly 36 includes a PF-resist cam surface 40 and a PF-resist follower pin 42 slidingly housed in a PF-resist channel 41 formed in joint body 12, engaged by normal contact with PF-resist cam surface 40 in plantarflexion. Follower pin 42 includes a collar 43 with a lower annular end face 37 (seen in FIG. 10A) that abuts or "bottoms out" against a generally upwardly facing annular bottom surface 39 (seen in FIG. 10A) of channel 41 to provide a fixed lower stop position of pin 42, as illustrated in FIGS. 9 and 10B. In addition, assembly 36 includes a PF range of motion ("ROM") limiter pin 44 inserted through a first rocker/PF-resist spring 46; tibial shank angle locking bolt 31, which slides over PF-resist spring 46; and a PF ROM set screw 48 threaded into locking bolt 31.

PF-resist channel bottom surface 39 limits the downward excursion of pin 42 so that pin 42 ceases to transmit a PF-resist biasing force to PF-resist cam surface 40 at the equilibrium angle of lower bar 17 shown in FIG. 9, and cam surface 40 loses contact with pin 42 when pivoted from the equilibrium angle in a dorsiflexion direction. Throughout the embodiments illustrated herein, a similar arrangement of a pin or ball bearing having a limited excursion in or from a channel in which it is housed is employed to isolate the lower bar from PF-resist torques (both preload and variable) when outside the active PF-resist range of angular motion, and from DF-resist torques (both preload and variable) when outside the active DF-resist range of angular motion. In addition, in the illustrated embodiments, the components are sized, shaped, and arranged so that the respective DF-resist and PF-resist active ranges of motion cannot overlap, because the PF-resist cam follower member bottoms out in its channel just before the DF-resist cam surface of the lower bar stirrup begins to displace the DF-resist cam follower member, and likewise, the DF-resist cam follower member bottoms out in its channel just before the PF-resist cam surface of the lower bar stirrup begins to displace the PF-resist cam follower member. Thus, the stirrup is in flush contact with both follower members in its neutral position, but at the same time isolated from biasing forces transmitted by either cam follower member until it begins to move in one direction or the other. Advantageously, this permits DF-resist adjustments (such as preload or ROM) to be made without affecting PF-resist adjustments, and vice versa, while at the same time avoiding any play in the joint between the active DF- and PF-resist ranges, thus assisting the wearer with midstance stability. In the event that some play is desired for a particular purpose or a particular individual wearer, this could be achieved, for example, by shortening the protruding portion of one or both follower members, or by receding one or both cam profiles of the stirrup, relative to those of the illustrated embodiments. Finally, it should be noted that isolating the lower bar from DF- and PF-resist forces outside of the respective desired ranges may be achieved in other ways without departing from the scope of the invention. For example, instead of an intervening rigid component (i.e., a follower/force transmission member), a portion of a spring/resistive element may be configured to contact part of the lower bar, subject to a fixed limitation on its movement toward the contacted part of the lower bar. Moreover, in the absence of preload, a "fixed stop" on the displacement of the lower bar contacting component need not take the form of an abutting fixed surface as in the illustrated embodiments, but may simply be the fully relaxed position of the free end of a compression spring having an opposite end fixed to the joint body, or of a rigid body that is fixedly attached to an end of a fully relaxed compression spring having an opposite end attached to the joint body. Thus, the term "fixed stop" will be understood as encompassing such a relaxed free end arrangement, and not only arrangements involving abutment against a fixed surface or other form of "stop member." In addition, the displacement path of whatever component contacts the lower bar need not be purely translational; it may instead be purely rotational or include both translation and rotation.

PF ROM set screw 48 serves to define an adjustable plantarflexion range of motion as a clearance between PF ROM limiter pin 44 and a selected "fixed" position of set screw 48, "fixed" in the sense that, though adjustable by turning, it is essentially immovable by linear forces transmitted from PF-resist spring 46. In addition to adjusting plantarflexion range of motion, PF ROM set screw 48 also serves to adjust the preload applied to PF-resist spring 46, as PF ROM limiter pin 44 and spring 46 are disposed in parallel between PF-resist follower pin 42 and PF ROM set screw 48. Thus, advancing PF ROM set screw 48 increases the preload of PF-resist spring 46 and reduces the range of plantarflexion pivotal movement of stirrup 14 relative to joint body 12, while retracting PF ROM set screw 48 decreases the preload of spring 46 and increases the range of plantarflexion pivotal movement of stirrup 14 relative to joint body 12. For a typical patient, PF-resist spring 46 may be adjusted to provide as little as 0 in-lb or as much PF-resist preload torque as can be provided by the spring through its active range. At the end of its active range and under maximum compression, the motion limiting stop exerts the maximum resistive torque bypassing the spring. Additional flexibility in torque ranges may be provided by substituting stiffer or softer springs, which is permitted in each of the illustrated embodiments by simply unscrewing a cap or adjustment/set screw.

Joint device 10 permits several additional ways of adjusting plantarflexion range of motion according to the invention. For example, the modular design of PF-resist assembly 36 advantageously permits the substitution of a longer or shorter PF ROM limiter pin for pin 44 (or if PF ROM limiter pin 44 is permanently joined to PF-resist follower pin 42 to form a single member, removal and replacement of the combined member with one having a longer or shorter ROM limiter portion corresponding to pin 44), as well as the insertion or removal of any of a plurality of spacers, such as rod-, disc-, or washer-like spacers (not shown) stacked above or below pin 44 in the interior of PF-resist spring 46. Any of the foregoing adjustments would change the angle of maximum permitted plantarflexion relative to the neutral ankle angle. Further, adding or removing one or more washers (not shown) in series with PF-resist spring 46 can compensate for a change in the preload of PF-resist spring 46 resulting from an adjustment of PF ROM set screw 48, thus providing a multistep plantarflexion range of motion adjustment independent of PF-resist preload and neutral ankle angle. Finally, in the illustrated embodiment, collar 43 abuts a lower end surface 45 of tibial shank angle locking bolt 31 at a fixed maximum range of plantarflexion motion, acting as a fallback or default plantarflexion stop member whenever PF ROM set screw 48 is retracted to a distance PFROM$_{adj}$ from the upper end face of PF ROM limiter pin 44 that is greater than a distance PFROM$_{max}$ between an upper surface 47 of collar 43 and lower end surface 45 of tibial shank angle locking bolt 31. Thus, in this embodiment, a clearance between collar 43 and lower end surface 45 serves to set a maximum limit on plantarflexion range of motion, which may, for example, permit no more than 14 degrees of plantarflexion movement from the sagittal tibial shank angle.

In addition, as will be described in more detail below, absolute plantarflexion range of motion can be adjusted by changing the tibial shank angle of upper bar 16 relative to joint body 12, i.e., by independently adjusting the equilibrium ankle alignment angle itself, without altering the kinematic relationship between stirrup 14 and joint body 12. It should be noted that changing the equilibrium angle in this manner produces not only an absolute PF ROM adjustment, but also an equal and opposite absolute DF ROM adjustment.

Respective primary and secondary PF load paths P$_{PF1}$, P$_{PF2}$ of a plantarflexion force F$_{PF}$ from stirrup 14 through PF-resist assembly 36 and ankle joint body 12 to upper bar 16 are illustrated in FIG. 10A. With reference to primary load path P$_{PF1}$ shown in the drawing, force F$_{PF}$ is applied by normal contact of PF-resist cam surface 40 on PF-resist follower pin 42 and transmitted through pin 42 to PF-resist spring 46, through PF-resist spring 46 to PF ROM set screw 48, through the threads of PF ROM set screw 48 to the inner threads of tibial shank angle locking bolt 31, through the outer threads of sagittal alignment locking bolt 31 to the inner threads of ankle joint body 12, and finally through ankle joint body 12 to upper bar 16. Until stirrup 14 is rotated in plantarflexion to the end of its plantarflexion range of motion, substantially all of force F$_{PF}$ is transmitted via primary load path P$_{PF1}$.

However, once PF-resist follower pin 42 "bottoms out" by traversing a maximum range of motion PFROM$_{max}$ so that its collar 43 abuts tibial shank angle locking bolt 31 (as shown in FIG. 10A), or an adjustable range of motion PFROM$_{adj}$ so that PF ROM limiter pin 44 abuts PF ROM set screw 48 (not shown, but refer to FIG. 19 for an illustration of the analogous secondary load path via an ROM limiter pin in an alternative joint device embodiment), any excess force then bypasses PF-resist spring 46 via a secondary load path P$_{PF2}$, which essentially provides a hard stop preventing any further plantarflexion.

Dorsiflexion Resistance and Ranges of Motion

DF-resist assembly 38 comprises a DF-resist cam surface 50 and a DF-resist follower pin 52 engaged by normal contact with DF-resist cam surface 50 when stirrup 14 is pivoted past the neutral position in the dorsiflexion direction. With reference to FIGS. 9, 10A, and 10B, it will be readily understood that the extent of downward excursion of a narrow lower portion of DF-resist follower pin 52 from a DF-resist channel formed in joint body 12 is limited by an annular flange portion of follower pin 52 abutting a bottom surface of the channel, in a manner similar to that described above in more detail with respect to PF-resist follower pin 42. Additionally, DF-resist assembly 38 includes a terminal stance ("TS") DF-resist spring 54 (which may also be referred to for brevity as a "terminal stance spring"); a second rocker DF-resist spring 56; and a DF-resist spring guide pin 58 extending through DF-resist springs 54 and 56 and a hole 61 in an upper end of a DF-resist cap 62; cap 62 being threaded into joint body 12. A washer 64 is shown as a spacer/coupling element between DF-resist springs 54 and 56.

Respective primary and secondary load paths through the components of DF-resist assembly 38 are best illustrated in FIG. 10B. With reference to a primary load path P$_{DF1}$ shown in the drawing, force F$_{DF}$ is applied by normal contact of DF-resist cam surface 50 on DF-resist follower pin 52 and transmitted through pin 52 to TS DF-resist spring 54, through TS DF-resist spring 54 to second rocker DF-resist spring 56, through second rocker DF-resist spring 56 to DF-resist cap 62, through the threads of DF-resist cap 62 to the threads of ankle joint body 12, and finally through joint body 12 to upper bar 16. Until stirrup 14 is rotated in dorsiflexion to the end of its second rocker range of motion, substantially all of force F$_{DF}$ is transmitted via primary load path $P_{DF1}$. However, once TS DF-resist spring 54 traverses a second rocker ROM clearance 2RROM (shown in FIG. 9), so that a washer 64 abuts an annular lower end face 65 of DF-resist cap 62, any excess force then bypasses second rocker DF-resist spring 56 and is instead transmitted via a secondary load path $P_{DF2}$ leading directly from TS DF-resist spring 54 into DF-resist cap 62.

Analogously to PF-resist assembly 36, DF-resist assembly 38 permits adjustment of a second rocker range of motion and a preload of second rocker DF-resist spring 56 by advancing (lowering) and withdrawing (raising) DF-resist cap 62 into and out of a tapped hole 60 in ankle joint body 12. In particular, advancing DF-resist cap 62 increases second rocker preload and decreases second rocker ROM, while withdrawing DF-resist cap 62 decreases second rocker preload and increases second rocker ROM. In one preferred embodiment, an active second rocker range of motion of up to about 10° and an active terminal stance range of motion of up to about 7° are permitted, for a total active DF range of motion of up to about 17°. A second rocker DF-resist spring 56 may be adjusted to provide as little as 0 in-lb preload torque and up to a desired amount, which may depend on the wearer's weight and strength and other clinical factors.

TS DF-resist spring 54 should typically provide on the order of up to about 10 times the torque, or more if desired, of second rocker DF-resist spring 56. Thus, the wearer of joint device 10 will feel a dramatic increase in supportive resistance to dorsiflexion when it is most needed, in an uppermost range of dorsiflexion leading up to terminal stance, just before the wearer's heel lifts off the ground.

A polyurethane bushing is a compact and economical candidate to serve as TS DF-resist spring 54, being capable of providing a substantial step up in resistance without requiring a diameter so large as to impinge the wearer's leg or ankle or otherwise render the device cumbersome to wear. A significant consideration for polyurethane springs is that, at the required frequency of about 1 to 2 dorsiflexion cycles per second, the compression ratio acting on a polyurethane spring must be less than about 15% to avoid pre-set or slow recoil/response. Polyurethane springs are comparatively large as well, but not as large as comparable coil springs would be.

Analysis of required dorsiflexion resist torque, using representative values for post-CVA (cerebrovascular accident) orthotic management from the literature, suggests that even nested helical compression springs may need to be excessively large to deliver the required torque for management of knee flexion in late stance. Machined springs are likely a functionally suitable alternative to polyurethane springs, but could be prohibitively expensive. Gas springs may also be a suitable alternative resistive element.

Neutral Sagittal Tibial Shank Angle Adjustment

Figure 3:
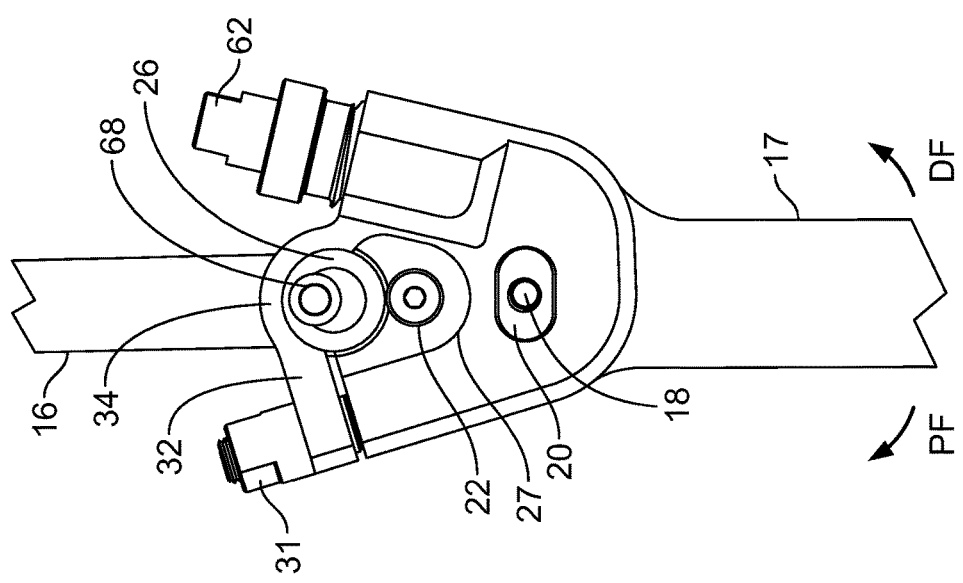
FIG. 3 is a right side elevation view of the device shown in FIG. 1.
Figure 2:
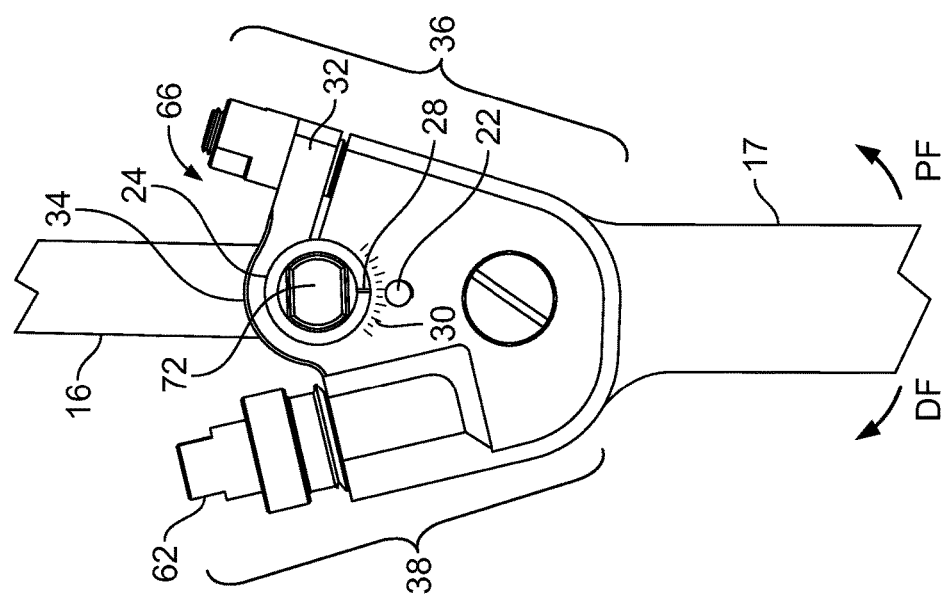
FIG. 2 is a left side elevation view of the device shown in FIG. 1.
Figure 4:
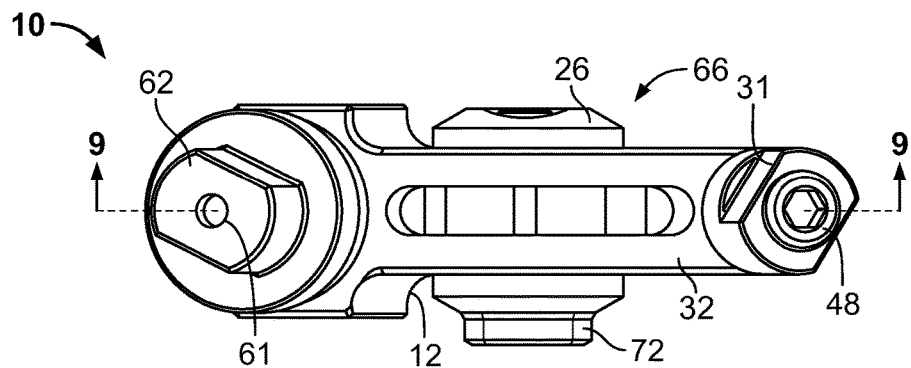
FIG. 4 is a top plan view of the device shown in FIG. 1.
Figure 5:
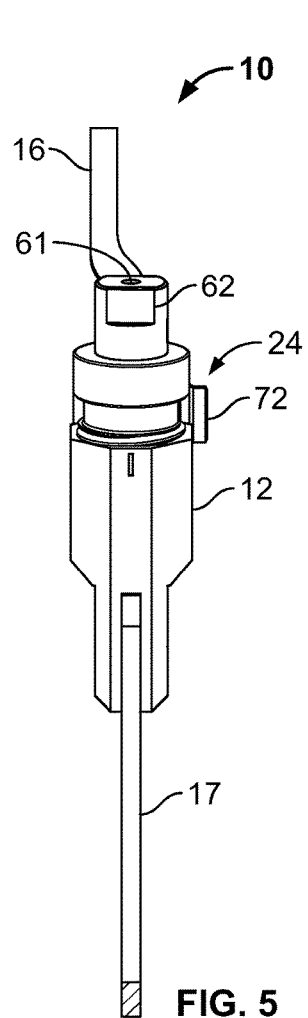
FIG. 5 is a front elevation view of the device shown in FIG. 1.
Figure 6:
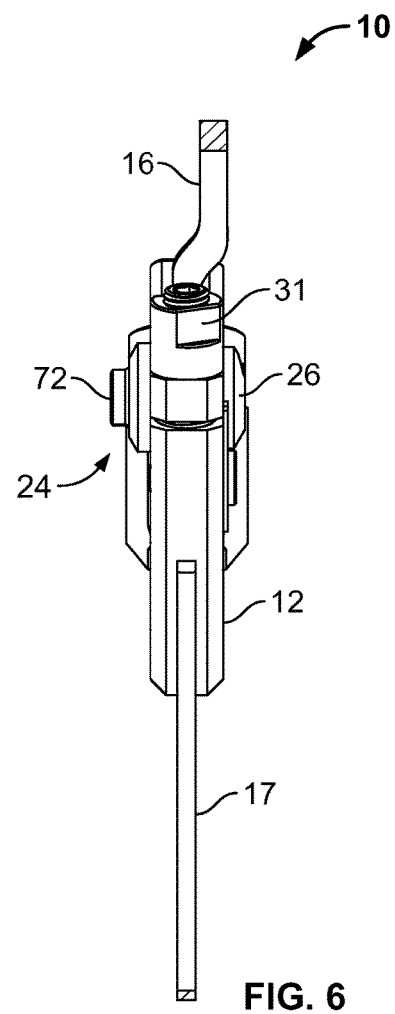
FIG. 6 is a rear elevation view of the device shown in FIG. 1.

A tibial shank angle adjustment assembly 66 for adjusting the angle of upper bar 16 in the sagittal plane, as best illustrated in FIGS. 2, 3, and 9, will now be described in detail. As mentioned above, tibial shank angle adjustment assembly 66 includes the aforementioned upper bar 16, upper bar pivot pin 22, tibial shank angle adjustment cam 24, tibial shank angle adjustment cam bushing 26, and tibial shank angle locking collar 34 that frictionally locks tibial shank angle adjustment cam 24 in place when tibial shank angle locking bolt 31 is tightened to apply a clamping force to clamping arm 32. With reference to FIGS. 2, 3 and 9, tibial shank angle adjustment cam 24 includes an eccentric tibial shank angle adjustment cam pin 68 fixed at an offset radial distance from a central axis of cam 24, so as to rotate about said central axis when cam 24 rotates in place in collar 34. In addition, cam pin 68 extends through a longitudinal cam slot 70 in upper bar 16.

Upper bar pivot pin 22 is disposed below tibial shank angle adjustment cam 24, and when upper bar 16 is in a twelve o'clock tibial shank angle adjustment position substantially aligned with lower bar 17, cam pin 68 is also disposed at the twelve o'clock position relative to the axis of cam 24, at its highest point in slot 70, and vertically aligned with the axes of cam 24 and upper bar pivot pin 22. From this position, the rotation of tibial shank angle adjustment cam 24 initially moves easily and amplifies the rotation of pivotal upper bar 16 away from the vertical tibial shank angle position, while amplification of rotation decreases and resistance to movement increases the farther upper bar 16 is rotated from the vertical position. To reflect this changing amplification, a step interval between equally spaced apart lines of scale 30 will decrease appropriately toward the extremes of shank angle adjustment. Alternatively, the spacing between neighboring scale lines indicating equal step intervals may increase toward the extremes.

Due to the increasing resistance to rotation of cam 24 as cam pin 68 is farther displaced from the twelve-o'clock position, a wearer or therapist grasping ankle joint body 12 with one hand and upper bar 16 with the other hand may easily be able to pivot upper bar 16 away from vertical alignment without a tool, but a tool (such as a special wrench) may be desired or needed to grip and rotate a bolt head 72 of cam 24 to and from larger angles of plantarflexion and dorsiflexion. On the other hand, the increasing resistance to rotation of cam 24 approaching the extremes of equilibrium angle adjustment advantageously helps to hold upper bar 16 at an inclined sagittal angle. Increased resistance to rotation is particularly beneficial, for example, when an inclined tibial shank angle is desired for the purpose of correcting a tendency of the wearer's ankle to flex in the opposite direction from vertical alignment, and/or for the purpose of exercising or strengthening a wearer's muscles that tend to urge the foot in the opposite direction toward vertical alignment. In either case, the device may be under nearly constant stress from the wearer's foot flexing or attempting to flex in said opposite direction, even when the wearer is at rest, tending to urge upper bar 16 back toward vertical alignment, and increased resistance to rotation of cam 24 will help to prevent upper bar 16 from budging.

In one embodiment, the tibial shank angle adjustment assembly 66 permits adjustment of upper bar 16 to a dorsiflexion angle $\Theta_1$, up to about +15°, or to a plantarflexion angle $\Theta_2$, up to about −15°, with respect to a vertical position of upper bar 16 relative to lower bar 17, seen in FIG. 9. This range considers not only typical biomechanical variances, which are about 10° dorsiflexion and −20° plantarflexion of functional range, but also the possibility that the clinician may want to asymmetrically offset the adjustment for a clinical purpose, such as correcting a malaligned ankle posture, compensating for a contracture (either in dorsiflexion or plantarflexion), or treating a joint contracture by using joint device 10 (or any other joint device according to the invention) as an active or static progressive component.

Second Illustrated Embodiment

Turning to FIGS. 11-19, another ankle joint device 74 is illustrated. Similarly to joint device 10 described above, joint device 74 includes a joint body 75, a pivotally mounted stirrup 77 comprising a PF-resist cam surface 79 and a DF-resist cam surface 81, an upper bar 83 generally configured for use as a lower leg splint mount, and a lower bar 85 integrally formed with stirrup 77 and extending downwardly therefrom, lower bar 85 being configured for attachment to a foot orthosis (not shown) or otherwise constrained to pivot in accordance with a wearer's bidirectional foot flexion. An upper bar pivot pin 22' and a lower bar stirrup bushing screw 18' and stirrup bushing 20' function analogously to the corresponding components of joint device 10.

Plantarflexion Resistance and Range of Motion

Joint device 74 includes substantially the same PF-resist assembly 36 as joint device 10, with like components labeled as in FIGS. 1-10B.

Dorsiflexion Resistance and Ranges of Motion

On the other hand, a DF-resist assembly 87 of joint device 74 differs somewhat in structure and function from assembly 38 of device 10. Most significantly, DF-resist assembly 87 provides a mechanism for adjusting dorsiflexion range of motion independently of second rocker preload. In particular, a second rocker ROM set screw 76 provides a hard stop to the range of motion of a second rocker ROM limiter pin 78 relative to a TS DF-resist spring hat 80. Set screw 76 and second rocker ROM limiter pin 78 fit without interference in the interior of a second rocker DF-resist spring 82, so that the second rocker range of motion is adjustable in a single step of turning set screw 76, without affecting a preload of second rocker DF-resist spring 82.

Figure 19:
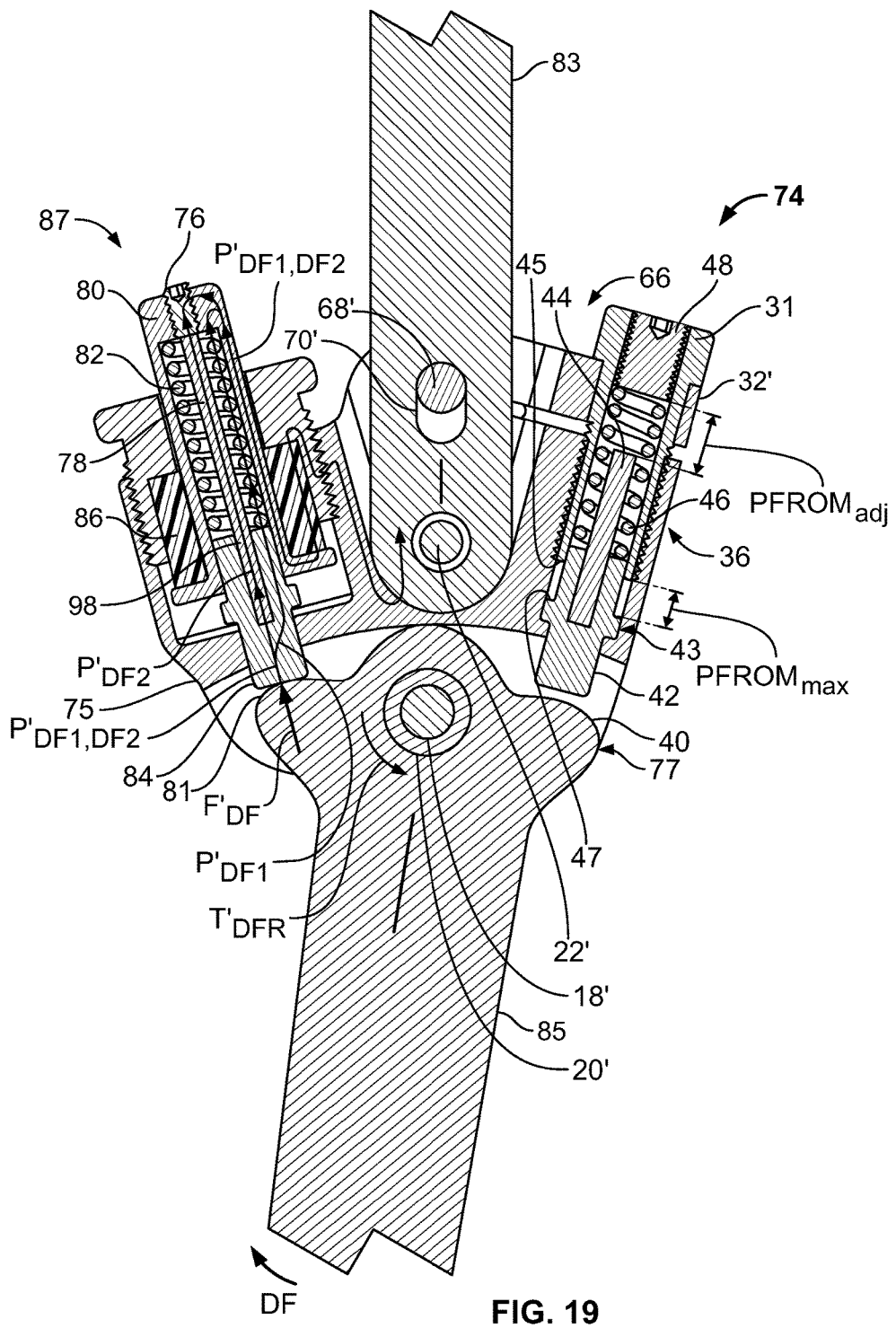
FIG. 19 is a left side sectional elevation view of the device shown in FIG. 12, depicting an orientation of the device at a terminal stance spring recruitment angle, at the end of a second rocker range of motion and within an overall dorsiflexion range of motion.

Respective primary and secondary load paths through the components of DF-resist assembly 87 of device 74 are best illustrated in FIG. 19. With reference to a primary dorsiflexion load path $P'_{DF1}$ shown in the drawing, force $F'_{DF}$ is applied by normal contact of DF-resist cam surface 81 on a DF-resist follower pin 84 and transmitted through pin 84 to second rocker DF-resist spring 82, through second rocker DF-resist spring 82 to a TS DF-resist spring hat 80, through TS-spring hat 80 to a TS DF-resist spring 86, through TS DF-resist spring 86 to a TS-resist cap 88 that is threaded into joint body 75, through the threads of TS-resist cap 88 to the threads of ankle joint body 75, and finally through joint body 75 to upper bar 83. When stirrup 77 begins to rotate in dorsiflexion from its neutral position (a position in which both PF-resist follower pin 42 and DF-resist follower pin 84 are bottomed out in their respective channels, isolating stirrup 77 from their respective biasing forces, as explained in more detail with respect to the first embodiment), and until stirrup 77 has rotated in dorsiflexion to the end of its second rocker range of motion, substantially all of force $F'_{DF}$ is transmitted via primary load path $P'_{DF1}$.

However, once DF-resist follower pin 84 traverses an adjustable second rocker ROM clearance $2RROM'_{adj}$ so that ROM limiter pin 78 abuts second rocker ROM set screw 76, or pin 84 traverses a maximum stop clearance $2RROM'_{max}$ so that an upper face of a DF-resist follower pin collar 90 abuts an annular lower end face 92 of TS-spring hat 80, any excess force then bypasses second rocker DF-resist spring 82 and is instead transmitted via a secondary load path leading from follower pin 84 through rigid elements into TS-spring hat 80 and then merging with primary load path $P'_{DF1}$. In FIG. 19, a secondary dorsiflexion load path $P'_{DF2}$ is illustrated which passes through DF-resist follower pin 84 to second rocker ROM limiter pin 78, through pin 78 to second rocker ROM set screw 76, and through outer threads of set screw 76 to inner threads of TS-spring hat 80, where it merges with primary load path $P'_{DF1}$ to rejoin a merged load path $P'_{DF1,DF2}$.

Figure 18:
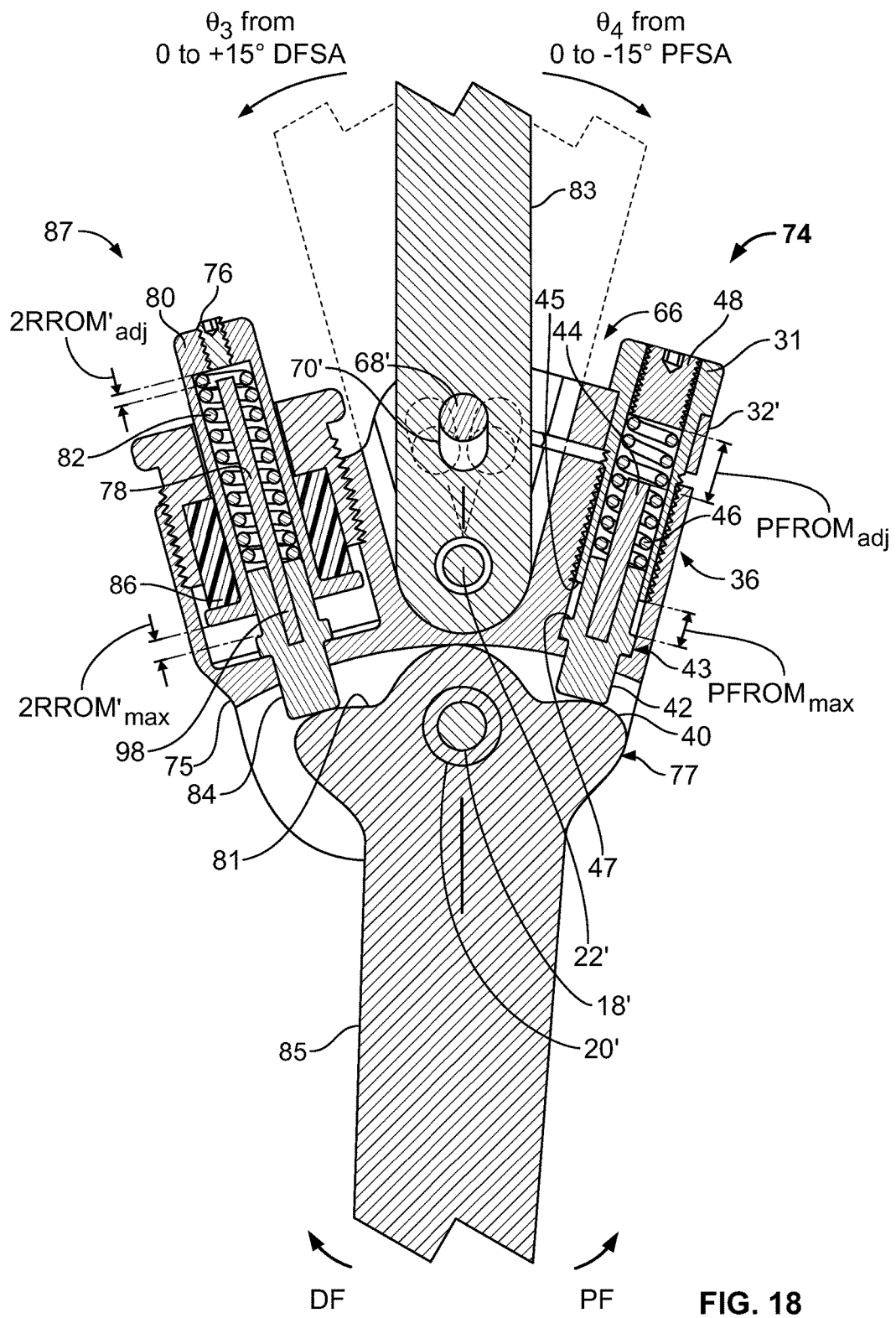
FIG. 18 is a left side sectional elevation view of the device shown in FIG. 11.

With reference to FIG. 18, when set screw 76 is sufficiently retracted so that primary stop clearance $2RROM'_{adj}$ exceeds maximum stop clearance $2RROM'_{max}$, an alternative secondary dorsiflexion load path (not shown) leads directly from follower pin collar 90 to TS-spring hat 80 to rejoin a merged load path. Advantages of imposing a fall-back maximum limit on a range of motion in such a manner, whether in plantarflexion or dorsiflexion, may include redundancy to address potential failure or inadvertent removal of set screw 76, protecting helical springs from overloading, protecting a wearer's joints from hyperflexion or a wearer from falling due to instability, and protecting other device components from impact damage, such as by one of the normal contact surfaces of the stirrup impacting a sharp corner of the joint body clevis.

Neutral Sagittal Tibial Shank Angle Adjustment

Neutral sagittal tibial shank angle adjustment is provided for substantially as in the first illustrated embodiment. Thus, upper bar 83 is pivotally mounted to joint body 75 to pivot about an upper bar pivot pin 22', and a similar tibial shank angle adjustment cam 24' is provided, with an alternative bolt head 72', cam pin 68', and cam bushing 26'; upper bar 83 including a cam slot 70' for slidingly receiving cam pin 68'. Shank angle adjustment cam 24' is locked by tightening locking bolt 31 to deflect a clamping arm 32' of a tibial shank angle locking collar 34'. In one embodiment, the maximum range of adjustment of tibial shank angle adjustment assembly 66 is from a dorsiflexion angle $\Theta_3$ up to about $+15°$ to a plantarflexion angle $\Theta_4$ up to about $-15°$, with respect to a vertical position of upper bar 83 relative to lower bar 85, seen in FIG. 18.

Third Illustrated Embodiment

Figure 20:
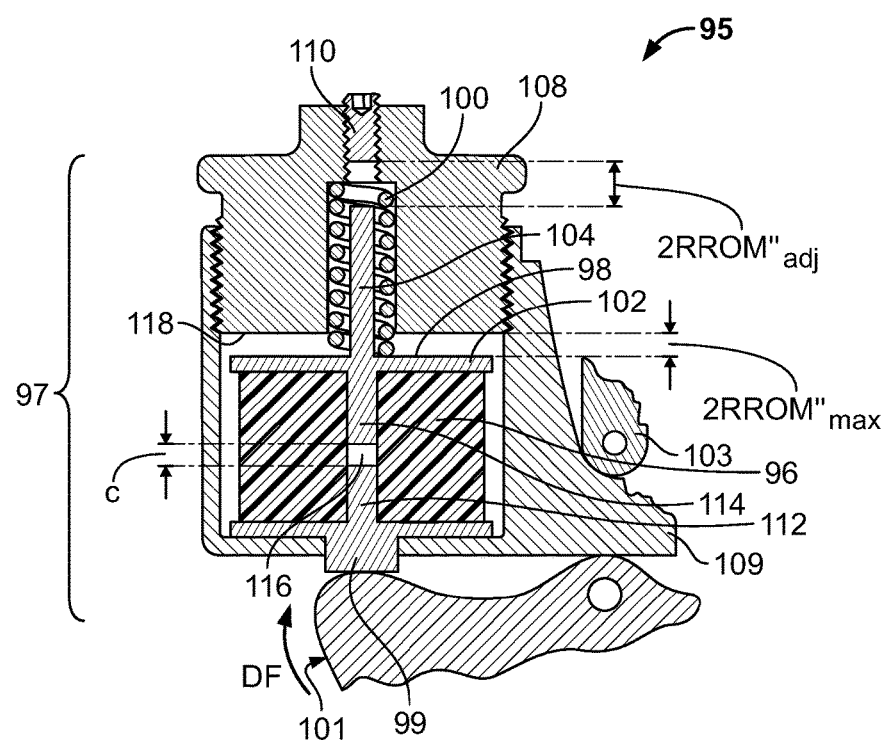
FIG. 20 is a left side fragmentary sectional elevation view of an ankle joint according to another embodiment of the invention.
Figure 21:
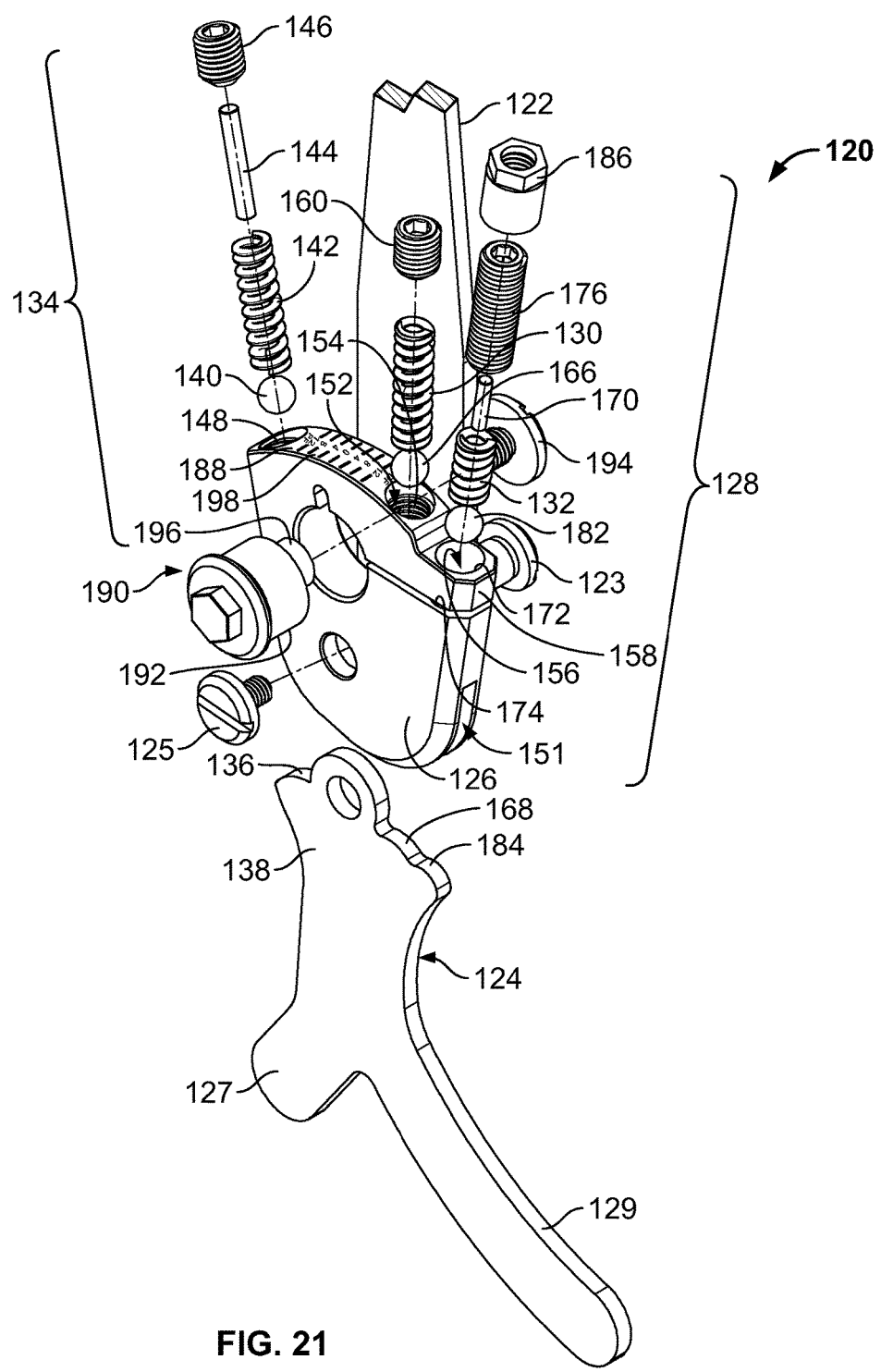
FIG. 21 is an exploded perspective view of an ankle joint according to another embodiment of the invention.
Figure 22:
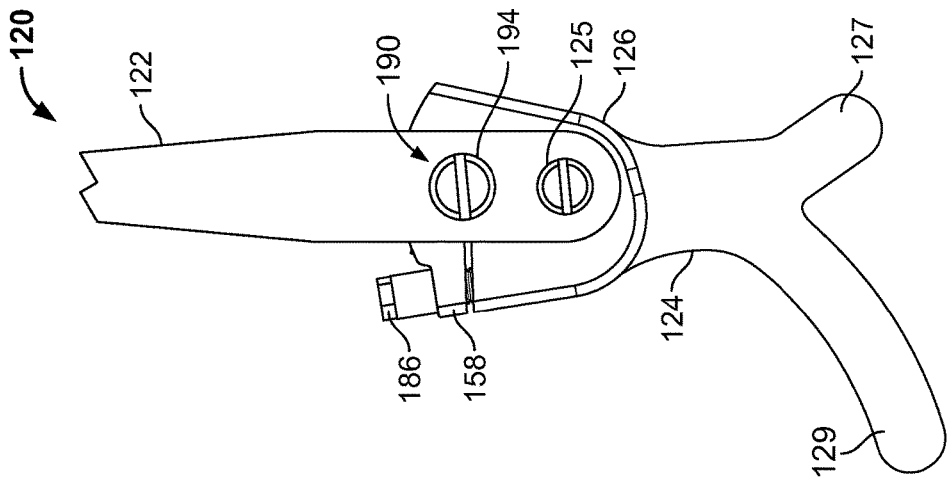
FIG. 22 is a right side elevation view of the assembled ankle joint of FIG. 21.
Figure 23:
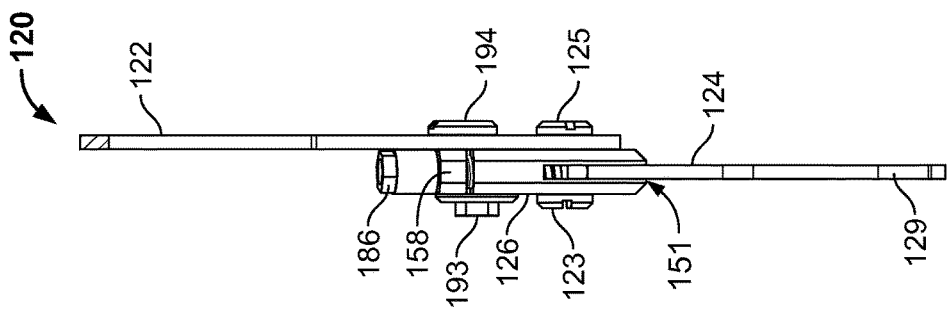
FIG. 23 is a front elevation view of the assembled ankle joint of FIG. 21.
Figure 24:
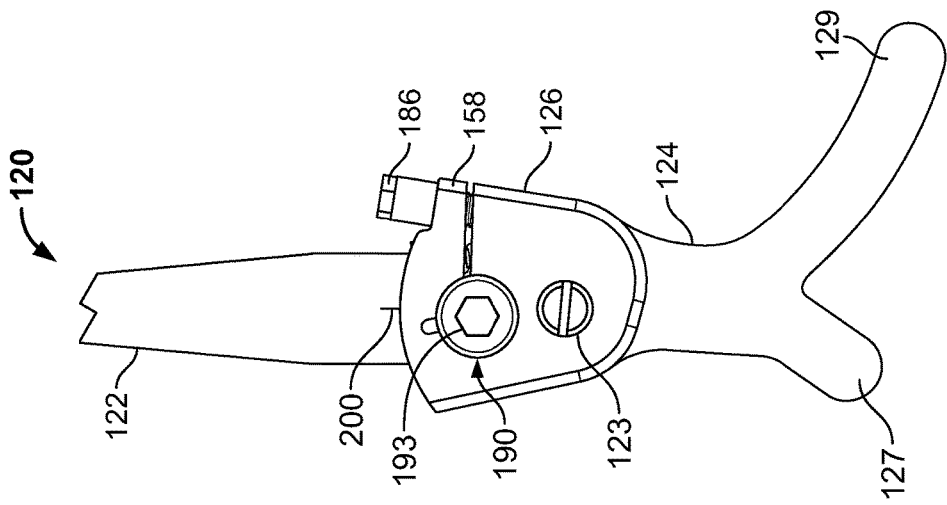
FIG. 24 is a left side elevation view of the assembled ankle joint of FIG. 21.
Figure 25:
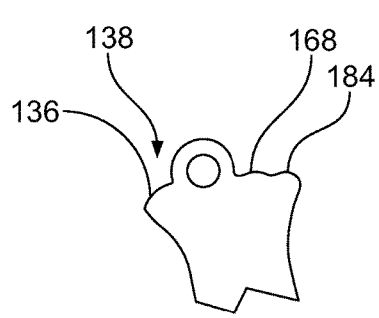
FIG. 25 is a right side fragmentary elevation view of a stirrup component of a lower bar of the ankle joint of FIG. 21.

Another ankle joint device 95 is partially shown in FIG. 20, to illustrate an alternative DF-resist assembly 97 for resisting a dorsiflexion load between a stirrup 101 and an upper bar 103. DF-resist assembly 97 includes a DF-resist follower pin 99 coupled to a bottom side of a TS DF-resist spring 96, a second rocker ROM-limiter member 98 coupled to a top side of TS DF-resist spring 96, a second rocker DF-resist spring 100 seated at its bottom end on a flange 102 of second rocker ROM-limiter member 98, guided by an inserted ROM-limiter pin 104 of ROM-limiter member 98, and seated at its top end on an annular bottom surface 106 of a DF-resist cap 108 threaded into an ankle joint body 109. Surface 106 surrounds a tapped hole receiving a second rocker ROM set screw 110 and accommodating the insertion of an upper end of ROM-limiter pin 104. The coupling of DF-resist follower pin 99 and ROM-limiter member 98 to TS DF-resist spring 96 maintains a clearance C between respective male coupling features 112, 114 of pin 99 and ROM limiter member 98, permitting TS DF-resist spring 96 to compress when further dorsiflexion load is applied at the end of the second rocker phase. Follower pin 99 and ROM limiter member 98 may either be permanently bonded (for example, by molding or adhesive applied to their respective annular flange surfaces) to TS DF-resist spring 96, or simply inserted into a hollow bore 116 thereof, preferably with a slight interference fit to hold the parts together. Thus, it will be understood that DF-resist assembly 97 provides for setting an adjustable second rocker range of motion $2RROM''_{adj}$ by turning second rocker ROM set screw 110, without affecting a second rocker preload, which may be adjusted by turning DF-resist cap 108, subject to a maximum second rocker range of motion $2RROM''_{max}$ between an annular bottom surface 118 of DF-resist cap 108, which is decreased as a second rocker preload is increased by turning DF-resist cap 108.

Fourth Illustrated Embodiment

Another ankle joint device 120 is illustrated in FIGS. 21-28. Ankle joint device 120 includes an upper bar 122 and a lower bar 124 pivotally connected to a joint body 126 by a shared pivot bushing 123 mounted by a pivot bolt 125. As illustrated in the drawings, lower bar 124 has a general "Y" shape with a heel arm 127 and an arch arm 129 being splayed so as to minimize or avoid impingement with a wearer's ankle and foot bones.

Figure 26:
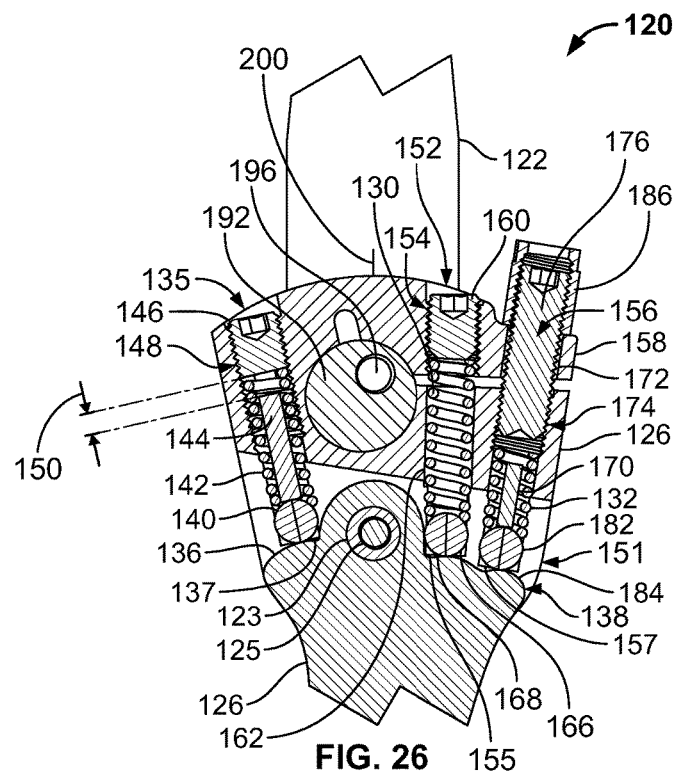
FIG. 26 is a right side fragmentary cross-sectional elevation view of the assembled ankle joint of FIG. 21.
Figure 27:
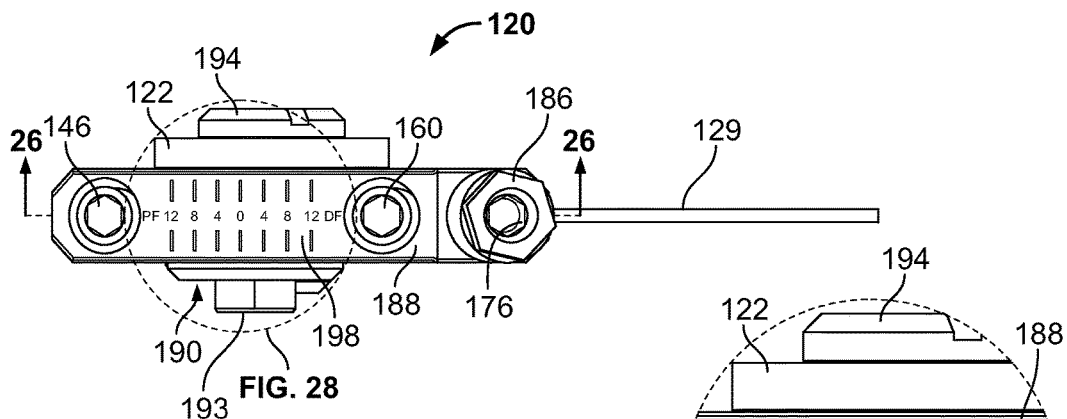
FIG. 27 is a top plan view of the assembled ankle joint of FIG. 21.
Figure 28:
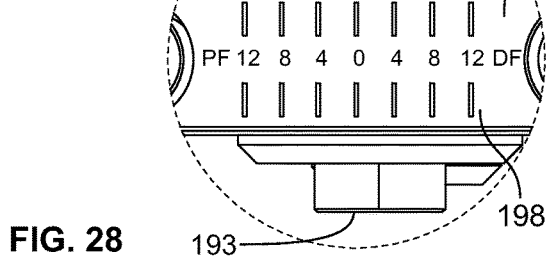
FIG. 28 is an enlarged view of a neutral sagittal tibial shank angle scale shown in the top plan view of FIG. 27.

Joint device 120 differs from the previously described embodiments in that its DF-resist assembly 128 includes a second rocker spring 130 and a TS DF-resist spring 132 that operate in parallel and are mounted side-by-side, as opposed to the nested, series second rocker and TS DF-resist spring assemblies described above; and upper bar 122 is mounted externally to joint body 126. Another difference is the substitution of cam follower ball bearings for cam follower pins in the respective DF-resist and PF-resist assemblies 128, 134. Ball bearings 140, 168, 182 are simply a preferred alternative to a follower pin as in the previously described embodiments, and these or any other suitable types of cam follower members may be employed interchangeably according to the invention in any of its embodiments for converting pivotal movement of a stirrup head to deflection of a suitable spring. Like the follower pins described above, ball bearings according to the invention are preferably made to bottom out in their respective channels by forming an appropriately sized and positioned opening at the bottom of the channel, to limit their travel so that the lower bar is isolated from PF-resist and DF-resist preload forces in its equilibrium position, as well as being isolated from any PF-resist forces in its DF-resist active angular range, and from any DF-resist forces in its PF-resist active angular range. With reference to FIG. 26, to facilitate the use of ball bearings as cam followers, a slot 151 is formed in joint body 126 for receiving stirrup head 138 overlaps a portion of each guide channel 135, 152, 156 in which the respective ball bearing 140, 168, 182 is housed, slot 151 having a smaller width than the ball diameters, and channels 135, 152, 156 having respective blind lower ends 137, 155, 157 except where the slot overlaps the channels, so that the ball bearings are retained in the channels and stirrup head 138 is permitted to invade the channels to displace the ball bearings and deflect their respective springs.

Plantarflexion Resistance and Range of Motion

A PF-resist assembly 134 of joint device 120, residing in a PF-resist spring guide channel 135 formed in joint body 126, includes a PF-resist lobe 136 of a lower bar stirrup head 138; a PF-resist ball bearing 140; a PF-resist spring 142; a PF ROM limiter pin 144 nested in parallel with PF-resist spring 142, each in load bearing communication with PF-resist ball bearing 140; and a PF-ROM set screw 146 threaded into a tapped upper portion 148 of PF-resist spring guide channel 135, set screw 146 bracing an upper end of PF-resist spring 142 and spaced from an upper end of PF-ROM set screw 146 by a clearance 150 to define a first rocker/plantarflexion range of motion. Aside from the use of PF-resist ball bearing 140 as a cam follower member, PF-resist assembly 134 is otherwise very similar to those described above, in that PF-ROM set screw 146 may be advanced to increase the preload of PF-resist spring 142 and reduce plantarflexion/first rocker range of motion and withdrawn to decrease preload and increase range of motion.

Dorsiflexion Resistance and Range of Motion

DF-resist assembly 128 of joint device 120 is more notably different from those previously described, in that it resides in two separate channels in joint body 126, namely, a second rocker spring guide channel 152 and a TS DF-resist spring guide channel 156 spaced forwardly of channel 152.

Second rocker spring guide channel 152 includes a tapped upper hole 154 formed in a tibial shank angle clamp arm 158 of joint body 126, for receiving a second rocker preload screw 160, and an untapped lower hole 162 formed in a portion of joint body 126 below clamp arm 158, for receiving and guiding the always active second rocker spring 130, operating in compression between preload screw 160 and a second rocker ball bearing 166 riding on a second rocker lobe 168 of stirrup head 138. In the depicted example, an ROM-limiter pin is omitted from channel 152. Although a pin could be used in channel 152 to limit dorsiflexion range of motion, this would have the drawback of potentially transmitting a large parasitic unlocking force to clamp arm 158 at the end of dorsiflexion range of motion, in a worst case potentially freeing upper bar 122 and permitting sudden hyperdorsiflexion that could injure the wearer. Thus, a DF ROM limiter pin 170 is preferably instead housed in TS DF-resist spring guide channel 156 in a load path that bypasses clamp arm 158, as described in the following paragraph.

TS DF-resist spring guide channel 156 includes an untapped upper hole 172 through tibial shank angle clamp arm 158 and a tapped lower hole 174 formed in a portion of joint body 126 below clamp arm 158, for receiving a second rocker/TS ROM set screw 176. Set screw 176 sets the recruitment angle of a TS DF-resist spring 132 housed in tapped lower hole 174 (thus defining a second rocker range of motion) and at the same time imposes a maximum limit on dorsiflexion range of motion by abutting a TS ROM limiter pin 170 nested within and in parallel relation to TS DF-resist spring 132. TS DF-resist spring 132 and TS ROM limiter pin 170 are both supported on a TS ball bearing 182 riding on a TS lobe 184 of stirrup head 138. Finally, a tibial shank angle lock nut 186 is tightened onto an upper end of second rocker/TS ROM set screw 176 to engage clamp arm 158, thus locking upper bar 122 at a desired tibial shank angle. Because lower hole 174 of TS DF-resist spring guide channel 156 is tapped and upper hole 172 is not, any force transmitted by TS DF-resist spring 132, as well as any excess force transmitted by TS ROM limiter pin 170 to set screw 176 bypasses clamp arm 158, is instead borne as a generally upward load by the portion of joint body 126 disposed below clamp arm 158. Accordingly, this load cannot have a parasitic unlocking effect. Preferably, TS DF-resist spring guide channel 156 is packed with damping grease to reduce acoustic noise associated with deflection of TS DF-resist spring 132 or initial contact of TS DF-resist spring 132 or TS ROM limiter pin 170 on second rocker/TS ROM set screw 176.

The springs of PF-resist assembly 134 and DF-resist assembly 128 as described above may be, for example, helical wire springs as depicted in the drawings, which are readily interchangeable with other stiffer or softer springs of like diameter, as desired for a broad range of clinical applications, by simply removing the appropriate set/adjustment screw 146, 160, 176 to remove and replace the respective spring 142, 130, 132. Similarly, PF ROM limiter pin 144 and TS ROM limiter pin 170 may be removed and replaced with longer or shorter pins as desired to make different respective ranges of motion possible.

Neutral Sagittal Tibial Shank Angle Adjustment

Upper bar 122 is mounted to joint body 126 in a similar fashion to the upper bars of the embodiments previously described. Upper bar 122 is mounted to a pivot bushing 123 shared with lower bar 124, as noted above, and is connected to a tibial shank angle adjustment cam 190 that is substantially similar to cam 24 described previously, including a cam bushing 192 (shown in FIG. 21) having an integral adjustment bolt head 193, a cam bolt 194, and an eccentric cam pin 196 (shown in FIG. 21). Cam pin 196 receives bolt 194, revolves around an axis of cam 190, and slides in a longitudinal cam slot (not shown) in upper bar 122 similar to cam slot 70 of upper bar 16, while cam 190 is locked by tightening lock nut 186 onto clamp arm 158 as noted above. However, unlike in the previously described embodiments, upper bar 122 is mounted to one side of joint body 126 instead of in a slot within a joint body.

Advantageously, this arrangement makes room in joint body 126 for second rocker spring channel 152, as well as affording a wearer or clinician full view of a top surface 188 of joint body 126 providing additional space for tibial shank angle indicia 198 to be printed, engraved, or otherwise applied thereon. Indicia 198 may cooperate with pointer indicia 200 on a side of upper bar 122 facing joint body 126 to indicate a tibial shank angle of upper bar 122 in the sagittal plane relative to lower bar 124.

Graphically Illustrated Gait Cycle

Figure 29:
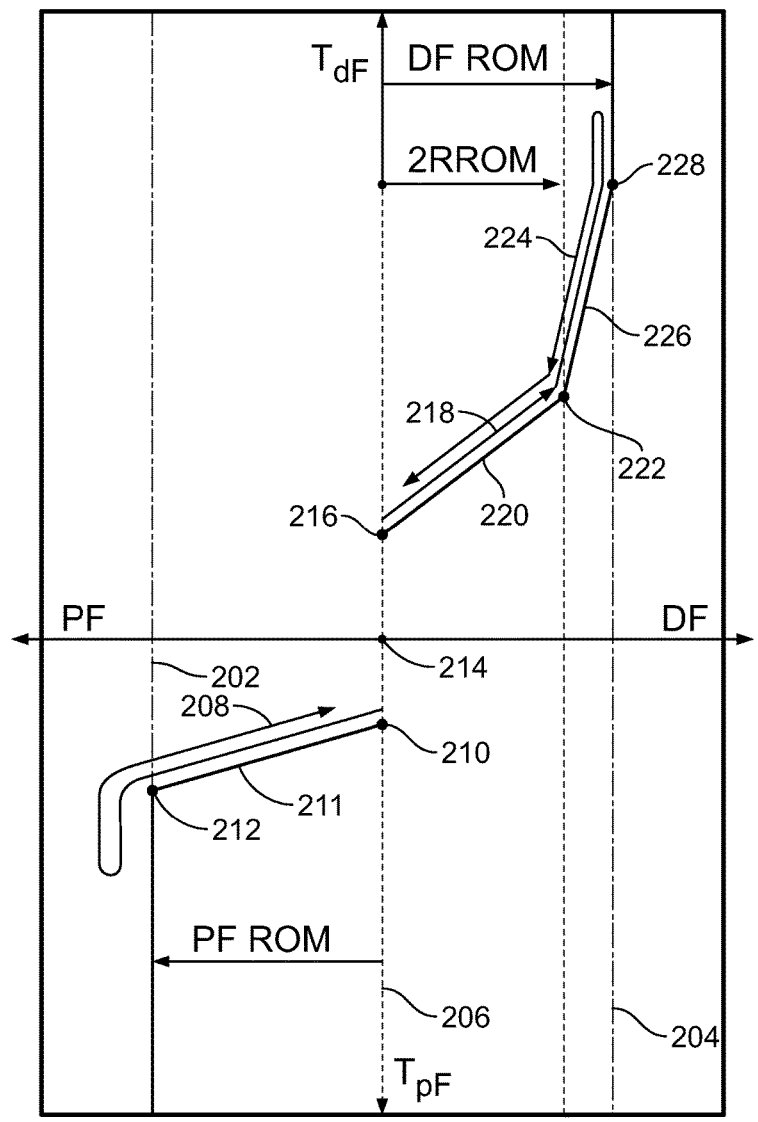
FIG. 29 is a graph depicting a particular representative plantarflexion torque response curve and a particular representative dorsiflexion torque response curve of a device according to the invention.

With reference to FIG. 29, an illustrative example of a gait cycle, proceeding along a particular representative plantarflexion torque response curve and a particular representative dorsiflexion torque response curve, is illustrated graphically with arrows for the first rocker (including any plantarflexion overload at a point of maximum plantarflexion permitted by the device), second rocker, and third rocker/terminal stance (including any dorsiflexion overload at a point of maximum dorsiflexion permitted by the device) phases of a wearer's gait in devices according to the invention. For purposes of this illustrative gait cycle and the various adjusted torque response curves illustrated in FIG. 30 discussed below, a linear torque-angle response is assumed for each spring; however, depending on the type of spring used, any modifications to the spring structure, such as staging or beveling the inner diameter of a polyurethane bushing spring, the shape of the stirrup cam surface, and other parameters, the torque-angle response could be made to be other than linear as desired.

Read clockwise from the bottom axis, the respective axes of the graph indicate plantarflexion torque $T_{pF}$, plantarflexion angle PF, dorsiflexion torque $T_{dF}$, and dorsiflexion angle DF. A maximum plantarflexion angle 202 is indicated by the dashed line toward the left of the figure, and a maximum dorsiflexion angle 204 is indicated by the dashed line toward the right of the figure, with respect to a tibial shank angle 206.

A first rocker phase 208 of a wearer's gait begins with a PF preload torque 210 (which may be zero) at tibial shank angle 206 at heel strike, proceeds along a first rocker torque response curve to a maximum PF torque 212 at maximum PF angle 202 corresponding to ball strike, which may be less than or equal to the PF range of motion permitted by the device. If the wearer plantarflexes to the maximum plantarflexion range of motion PF ROM permitted by the device and continues to bear against the device in plantarflexion, any additional load will be borne by substantially rigid device components so that the torque response curve becomes essentially vertical. The gait cycle then returns along the same torque response curve to PF preload torque 210, if any. If there is a PF preload torque, the response torque then drops to zero at midstance 214, followed by jumping to DF second rocker preload torque 216, if any. It will be noted that if either preload torque 210, 216 is zero, the corresponding torque response curve will simply begin at the origin of the graph shown.

In a second rocker dorsiflexion phase 218, the device torque response then proceeds along a second rocker torque response curve 220 to a second rocker/terminal stance transition torque 222. At this point, corresponding to the limit of second rocker range of dorsiflexion motion 2RROM permitted by the device as adjusted, the terminal stance spring is recruited.

As the dorsiflexion angle continues to increase in a terminal stance phase 224, the resulting TS response curve 226 is steeper than second rocker response curve 220, continuing to a maximum TS (or combined DF-resist, in the case of parallel DF-resist springs) spring torque 228. In terminal stance phase 224, dorsiflexion of the wearer's foot to the maximum dorsiflexion range of motion DF ROM may or may not occur, but with reference to FIG. 30, assuming that the wearer does reach maximum dorsiflexion and continues to bear against the device, the torque response curve will become substantially vertical until the dorsiflexion forces begin to relax, and the gait cycle returns along the same path toward the graph origin to begin again.

Illustrative Adjusted Plantarflexion and Dorsiflexion Torque Response Curves

Figure 30:
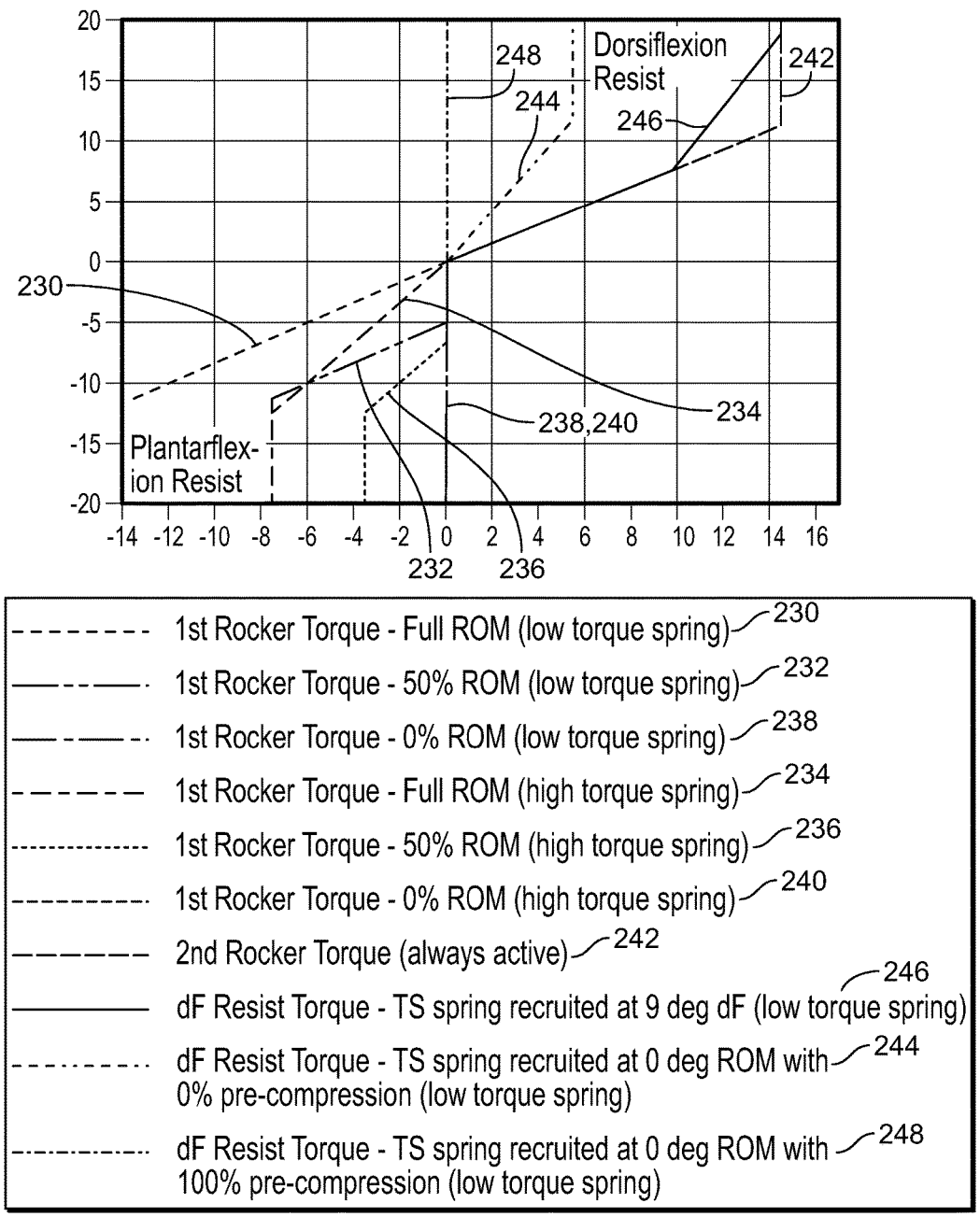
FIG. 30 is a graph depicting the effects of certain adjustments and component substitutions on representative plantarflexion and dorsiflexion torque response curves of a device according to the invention.

Turning to FIG. 30, several illustrative plantarflexion-resist and dorsiflexion-resist torque response curves are shown to illustrate the torque response effect of adjustments to ranges of motion, TS DF-resist spring preloading, and spring selection. The curves depicted represent the behavior of the fourth illustrated embodiment of joint device 120, though it will be readily understood that certain features of the curves apply to all four illustrated embodiments. For purposes of this illustration, the second rocker preloads are assumed to be zero; they could be represented as nonzero by simply shifting the curve in question upward by the value of the desired second rocker preload. The origin of the graph represents the device at the tibial shank angle with no active resistance torque applied, the positive angles and positive torques (in N-m) in the upper right quadrant represent angles of dorsiflexion relative to the tibial shank angle and dorsiflexion-resist torques, and the negative angles and negative torques in the lower left quadrant represent angles of plantarflexion relative to the tibial shank angle and plantarflexion-resist torques.

Referring to the lower left quadrant and comparing respective full and 50% range of motion first rocker low torque spring curves 230, 232, and first rocker high torque spring curves 234, 236, one sees that the curves generally shift down and to the right as range of motion is cut in half, which in the illustrated embodiments also entails increasing a first rocker preload (the y-intercepts of 50% ROM curves 232, 236) to half of the peak first rocker spring torque. The respective first rocker low and high torque 0% ROM curves 238, 240 are simply vertical lines extending downwardly from the origin, as 0% range of motion means that plantarflexion is essentially prevented for any plantarflexion torque that could be expected to come from a human wearing the device.

Referring to the upper right quadrant, a second rocker resistance curve 242 reflects the behavior of always active second rocker spring 130 of device 120, to which a second rocker preload could be applied by shifting any dF-resist curve upward by the magnitude of the preload, as noted above. A dF-resist curve of device 120 will follow curve 242 up to the angle of recruitment of TS DF-resist spring 132 and then continue along a steeper slope equal to the sum of the respective spring rates of second rocker spring 130 and TS DF-resist spring 132, now engaged in parallel. Thus, a dF-resist curve 244 with a 0% pre-compressed TS DF-resist spring 132 recruited at 0° departs from the origin with a uniform steep slope until TS ROM limiter pin 170 bottoms out and the slope becomes vertical, whereas a dF-resist curve 246 with a 0% pre-compressed TS DF-resist spring 132 recruited at 9° follows second rocker resistance curve 242 up to 9° dorsiflexion, followed by departing from curve 242 at 9° with the same slope as curve 244. Finally, similarly to the 0% plantarflexion ROM curves 238, 240, a 100% pre-compressed TS DF-resist spring recruited at 0° dorsiflexion (i.e., TS ROM set screw 176 is tightened until it meets TS ROM limiter pin 170 with TS ball bearing 182 bottomed out in its channel 156) results in preventing essentially any dorsiflexion from the tibial shank angle, corresponding to a dF-resist curve 248 that is simply a vertical line extending upwardly from the origin.

Summary of Illustrative Performance Specifications

Typical performance specifications of devices according to the invention, also mentioned above in discussing each separate function/assembly of device 10, are as follows: A representative tibial shank angle/equilibrium ankle angle adjustment range is about +/−15° from a vertical angle of an upper bar or other lower leg attachment member. A typical active plantarflexion resist range of motion is up to about (−)14° of plantarflexion. A typical active second rocker range of motion is up to about (+)10° of dorsiflexion, and a typical active terminal stance range of motion is up to about (+)7° of additional dorsiflexion, for up to about 17° of total dorsiflexion. Plantarflexion and dorsiflexion resisting torques are typically functionally isolated, as is the case in all of the illustrated embodiments, such that torque adjustments and adjustments to preload torques for dorsiflexion resist are completely isolated and functionally independent from torque adjustments and adjustments to preload torques for plantarflexion resist.

Materials and Construction

Components of devices according to the invention may be formed of steel, aluminum, titanium, polymer composite or other material suitable for orthotic devices. With the exception of the polyurethane bushing TS DF-resist springs illustrated in the first through third embodiments, springs employed in the illustrated embodiments may typically be composed of spring steel wire or other metallic or non-metallic alloys as are suitable to generate torques consistent with performance requirements of the joint component for orthotic service. Machined springs according to the invention may typically be made from a metal bar starting material, but they may be formed of any suitable machinable material, including some plastics. Additionally, springs comprised of gas cylinders, such as nitrogen gas springs, for example, may be substituted for the springs used in the illustrated embodiment or employed in other embodiments not shown.

Variations of the Invention

While the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An ankle joint device comprising
a joint body;
an attachment member pivotally connected to the joint body for pivotal movement in a dorsiflexion direction and a plantarflexion direction opposite to the dorsiflexion direction;
a plantarflexion resistance spring configured to bias the attachment member in the dorsiflexion direction relative to the joint body when the attachment member is within a plantarflexion resistance spring active angular range, the plantarflexion resistance spring active angular range beginning at a plantarflexion resistance spring recruitment angle and increasing in plantarflexion angle therefrom;
an initial dorsiflexion resistance spring configured to bias the attachment member in the plantarflexion direction relative to the joint body when the attachment member is within an initial dorsiflexion resistance spring active angular range, the initial dorsiflexion resistance spring active angular range beginning at an initial dorsiflexion resistance spring recruitment angle and increasing in dorsiflexion angle therefrom; and
a terminal stance dorsiflexion resistance spring configured to bias the attachment member in the plantarflexion direction relative to the joint body when the attachment member is within a terminal stance dorsiflexion resistance spring active angular range; the terminal stance dorsiflexion resistance spring active angular range having at least a terminal stance dorsiflexion resistance spring recruitment angle and an angular range increasing in dorsiflexion therefrom, the terminal stance dorsiflexion resistance spring recruitment angle being greater in dorsiflexion than the initial dorsiflexion resistance spring recruitment angle.

2. The device of claim 1, the initial dorsiflexion resistance spring and the terminal stance dorsiflexion resistance spring being comprised in a single spring having a higher effective spring rate in the terminal stance dorsiflexion resistance spring active angular range than in a range of angles between the initial dorsiflexion resistance spring recruitment angle and the terminal stance dorsiflexion resistance spring recruitment angle.

3. The device of claim 1, wherein the plantarflexion resistance spring active angular range has an angle of greatest plantarflexion and the initial dorsiflexion resistance spring active angular range has an angle of greatest dorsiflexion, the attachment member being positionable in at least one neutral angle relative to the joint body in which a net biasing torque transmitted to the attachment member from the joint body is zero, the neutral angle being between the angle of greatest plantarflexion in the plantarflexion resistance spring active angular range and the angle of greatest dorsiflexion in the initial dorsiflexion resistance spring active angular range.

4. The device of claim 3, the neutral angle being equal to the plantarflexion resistance spring recruitment angle and equal to the initial dorsiflexion resistance spring recruitment angle.

5. The device of claim 3, wherein substantially no biasing torque is transmitted to the attachment member at the neutral angle from any of the plantarflexion resistance spring, the initial dorsiflexion resistance spring, and the terminal stance dorsiflexion resistance spring.

6. The device of claim 3, further comprising
a dorsiflexion resistance transmission member operatively connected between the joint body and the attachment member and biased to move toward the attach member in a direction that opposes dorsiflexion movement of a dorsiflexion-resist contact surface of the attachment member;

a fixed dorsiflexion-resist stop restricting said dorsiflexion opposing movement toward the attachment member beyond a neutral position of the dorsiflexion-resist transmission member where the dorsiflexion-resist transmission member abuts the dorsiflexion-resist contact surface of the attachment member disposed at said neutral angle, the fixed dorsiflexion-resist stop not contacting the dorsiflexion-resist transmission member when the dorsiflexion-resist transmission member is not in its neutral position;

a plantarflexion-resist transmission member operatively connected between the joint body and the attachment member and biased to move toward the attachment member in a direction that opposes plantarflexion movement of a plantarflexion-resist contact surface of the attachment member; and a fixed plantarflexion-resist stop restricting said plantarflexion opposing movement toward the attachment member beyond a neutral position of the plantarflexion-resist transmission member where the plantarflexion-resist transmission member abuts the plantarflexion-resist contact surface of the attachment member disposed at said neutral angle, the fixed plantarflexion-resist stop not contacting the plantarflexion-resist transmission member when the plantarflexion-resist transmission member is not in its neutral position.

7. The device of claim 1, the initial dorsiflexion resistance spring configured to relay an initial dorsiflexion resisting force transmitted from the ankle joint body to the attachment member by a load path avoiding the terminal stance dorsiflexion resistance spring and extending through the ankle joint body to the attachment member.

8. The device of claim 1, the initial dorsiflexion resistance and terminal stance dorsiflexion resistance springs being operatively connected in series between the attachment member and the joint body when the attachment member is positioned between the initial dorsiflexion resistance spring recruitment angle and the terminal stance dorsiflexion resistance spring recruitment angle.

9. The device of claim 1, further comprising an initial range of dorsiflexion limiting member being engaged at the terminal stance dorsiflexion resistance spring recruitment angle to transmit a terminal dorsiflexion resisting force from the terminal stance dorsiflexion resistance spring to the attachment member by a load path avoiding the initial dorsiflexion resistance spring, and to convert any further dorsiflexion movement of the attachment member to deflection of the terminal stance dorsiflexion resistance spring, the load path extending through the ankle joint body to the attachment member.

10. The device of claim 9, said initial range of dorsiflexion limiting member being spaced by a clearance from a terminal stance dorsiflexion resistance spring engagement surface when the attachment member is at the initial dorsiflexion resistance spring recruitment angle, the terminal stance dorsiflexion resistance spring being deflectable to produce said terminal dorsiflexion resisting force by movement of said terminal stance dorsiflexion resistance spring engagement surface impelled by movement of said initial range of dorsiflexion limiting member against said terminal stance dorsiflexion resistance spring engagement surface, and the attachment member configured to move the initial range of dorsiflexion limiting member into contact with the terminal stance dorsiflexion resistance spring engagement surface when moved from the initial dorsiflexion resistance spring recruitment angle to the terminal stance dorsiflexion resistance spring recruitment angle.

11. The device of claim 9, the initial dorsiflexion resistance spring being a resistive element, disposed to be loaded in compression by dorsiflexion movement beyond the initial dorsiflexion resistance spring recruitment angle, and the initial range of dorsiflexion limiting member being an elongate range of dorsiflexion limiting rod disposed in an interior channel extending through the initial dorsiflexion resistance spring.

12. The device of claim 10, the terminal stance dorsiflexion resistance spring engagement surface being a surface of a terminal stance dorsiflexion resistance spring engagement member that is mounted for adjustment to any fixed position within an adjustable range of fixed positions relative to an attachment member engaging end of the terminal stance dorsiflexion resistance spring, said clearance between the initial range of dorsiflexion limiting member and the terminal stance dorsiflexion resistance spring engagement surface at the initial dorsiflexion resistance spring recruitment angle being adjustable by adjusting said fixed position of the terminal stance dorsiflexion resistance spring engagement member.

13. The device of claim 12, said fixed position of the terminal stance dorsiflexion resistance spring engagement member being adjustable without changing a force load on the terminal stance dorsiflexion resistance spring at the initial dorsiflexion resistance spring recruitment angle.

14. The device of claim 10, the terminal stance dorsiflexion resistance spring engagement surface being maintained in a fixed position relative to an attachment member engaging end of the terminal stance dorsiflexion resistance spring, a position of the terminal stance dorsiflexion resistance spring engagement surface being adjustable by adjusting a position of a joint body engaging end of the terminal stance dorsiflexion resistance spring relative to the joint body.

15. The device of claim 1, further comprising a first initial range of dorsiflexion limiting member spaced by a first clearance from a first terminal stance dorsiflexion resistance spring engagement surface when the attachment member is at the initial dorsiflexion resistance spring recruitment angle, the terminal stance dorsiflexion resistance spring being deflectable to produce a terminal dorsiflexion resisting force by movement of said first terminal stance dorsiflexion resistance spring engagement surface, the first terminal stance dorsiflexion resistance spring engagement surface being fixed relative to an attachment member engaging end of the terminal stance dorsiflexion resistance spring; and a second initial range of dorsiflexion limiting member spaced by a second clearance from a second terminal stance dorsiflexion resistance spring engagement surface when the attachment member is at the initial dorsiflexion resistance spring recruitment angle, the terminal stance dorsiflexion resistance spring being deflectable to produce a second terminal dorsiflexion resisting force by movement of said second terminal stance dorsiflexion resistance spring engagement surface, the second terminal stance dorsiflexion resistance spring engagement surface being configured to maintain a fixed position relative to an attachment member engaging end of the terminal stance dorsiflexion resistance spring when subjected to a force in a direction of movement impelled by dorsiflexion movement of the attachment member, said fixed position of the second terminal stance dorsiflexion resistance spring engagement surface being adjustable relative to a position of a joint body engaging end of the terminal stance dorsiflexion resistance spring;

wherein the attachment member is configured to move the first initial range of dorsiflexion limiting member toward the first terminal stance dorsiflexion resistance spring engagement surface and the second initial range of dorsiflexion limiting member toward the second terminal stance dorsiflexion resistance spring engagement surface upon further dorsiflexion movement of the attachment member from the initial dorsiflexion resistance spring recruitment angle; and the terminal stance dorsiflexion resistance spring recruitment angle is an angle of the attachment member at which one of the first initial range of dorsiflexion limiting member and the second initial range of dorsiflexion limiting member contacts the respective first or second terminal stance dorsiflexion resistance spring engagement surface.

16. The device of claim 1, further comprising a stirrup head integral to the attachment member, the stirrup head comprising a dorsiflexion cam surface and a plantarflexion cam surface;

a dorsiflexion follower member mounted for linear movement relative to the joint body; and a plantarflexion follower member mounted for linear movement relative to the joint body;

the dorsiflexion cam surface, when in the active angular range of the initial dorsiflexion resistance spring or the terminal stance dorsiflexion resistance spring, engaging the dorsiflexion follower member in normal contact so that dorsiflexion rotation of the dorsiflexion cam surface produces a loading translation of the dorsiflexion follower member, resulting in increased dorsiflexion resistance loading of at least one of the initial dorsiflexion resistance spring and the terminal stance dorsiflexion resistance spring, and plantarflexion rotation of the dorsiflexion cam surface produces an unloading translation of the dorsiflexion follower member, resulting in decreased dorsiflexion resistance loading of at least one of the initial dorsiflexion resistance spring and the terminal stance dorsiflexion resistance spring; and the plantarflexion cam surface, when in the active angular range of the plantarflexion resistance spring, engaging the plantarflexion follower member in normal contact so that plantarflexion rotation of the plantarflexion cam surface produces a loading translation of the plantarflexion follower member, resulting in increased plantarflexion resistance loading of the plantarflexion resistance spring, and dorsiflexion rotation of the plantarflexion cam surface produces an unloading translation of the plantarflexion follower member, resulting in decreased plantarflexion resistance loading of the plantarflexion resistance spring.

17. The device of claim 1, the initial dorsiflexion resistance spring and the terminal stance dorsiflexion resistance spring being linear compression springs mounted side-by-side in parallel operative engagement between the attachment member and the joint body.

18. The device of claim 17, the terminal stance dorsiflexion resistance spring being mounted to apply a dorsiflexion-resist force to the attachment member at a point farther displaced from a pivotal axis of the attachment member than a point of application of a dorsiflexion resist force applied by the initial dorsiflexion resistance spring to the attachment member.

19. The device of claim 1, further comprising a second attachment member pivotally connected to the ankle joint body about a generally horizontal axis; and a second attachment member locking mechanism operable to lock the second attachment member at a selected angle relative to the ankle joint body;

one of the attachment member and the second attachment member being configured for attachment to a lower leg of a human wearer of the device, and the other being configured for attachment to a foot of a human wearer of the device.

20. A method of making an ankle joint device, comprising forming an assembly of a joint body, an attachment member, a plantarflexion resistance spring, an initial dorsiflexion resistance spring, and a terminal stance dorsiflexion resistance spring;

pivotally connecting the attachment member to the joint body for pivotal movement in a dorsiflexion direction and a plantarflexion direction opposite to the dorsiflexion direction;

configuring the plantarflexion resistance spring to bias the attachment member in the dorsiflexion direction relative to the joint body when the attachment member is within a plantarflexion resistance spring active angular range, the plantarflexion resistance spring active angular range beginning at a plantarflexion resistance spring recruitment angle and increasing in plantarflexion angle therefrom;

configuring the initial dorsiflexion resistance spring to bias the attachment member in the plantarflexion direction relative to the joint body when the attachment member is within an initial dorsiflexion resistance spring active angular range, the initial dorsiflexion resistance spring active angular range beginning at an initial dorsiflexion resistance spring recruitment angle and increasing in dorsiflexion angle therefrom; and configuring the terminal stance dorsiflexion resistance spring to bias the attachment member in the plantarflexion direction relative to the joint body when the attachment member is within a terminal stance dorsiflexion resistance spring active angular range, the terminal stance dorsiflexion resistance spring active angular range having at least a terminal stance dorsiflexion resistance spring recruitment angle and an angular range increasing in dorsiflexion therefrom, the terminal stance dorsiflexion resistance spring recruitment angle being greater in dorsiflexion than the initial dorsiflexion resistance spring recruitment angle.

21. A method of supporting an ankle of a human in a range of dorsiflexion and plantarflexion motions, using an ankle joint device comprising a joint body, an attachment member pivotally connected to the joint body for pivotal movement relative to the joint body in the dorsiflexion direction and the plantarflexion direction opposite to the dorsiflexion direction, a plantarflexion resistance spring configured to bias the attachment member in the dorsiflexion direction relative to the joint body when the attachment member is within a plantarflexion resistance spring active angular range, the plantarflexion resistance spring active angular range beginning at a plantarflexion resistance spring recruitment angle and increasing in plantarflexion angle therefrom, an initial dorsiflexion resistance spring configured to bias the attachment member in the plantarflexion direction relative to the joint body when the attachment member is within an initial dorsiflexion resistance spring active angular range, the initial dorsiflexion resistance spring active angular range beginning at an initial dorsiflexion resistance spring recruitment angle and increasing in dorsiflexion angle therefrom, and a terminal stance dorsiflexion resistance spring configured to bias the attachment member in the plantarflexion direction relative to the joint body when the attachment member is within a terminal stance dorsiflexion resistance spring active angular range, the terminal stance dorsiflexion resistance spring active angular range having at least a terminal stance dorsiflexion resistance spring recruitment angle and an angular range increasing in dorsiflexion therefrom, the terminal stance dorsiflexion resistance spring recruitment angle being greater in dorsiflexion than the initial dorsiflexion resistance spring recruitment angle, the method comprising:
- attaching the attachment member to one of a foot and a lower leg corresponding to said ankle; and
- attaching the joint body to the other of the foot and the lower leg, the attached attachment member being configured to move in said dorsiflexion direction relative to the attached joint body when the human's foot dorsiflexes and in said plantarflexion direction relative to the attached joint body when the human's foot plantarflexes.

22. The device of claim 6, wherein the dorsiflexion-resist stop abuts the dorsiflexion resistance transmission member at said neutral angle and does not abut the dorsiflexion resistance transmission member when the attachment member is at a dorsiflexion angle greater than the initial dorsiflexion resistance spring recruitment angle and is in contact with the dorsiflexion resistance transmission member, and the plantarflexion-resist stop abuts the plantarflexion resistance transmission member at said neutral angle and does not abut the plantarflexion resistance transmission member when the attachment member is at a plantarflexion angle greater than the plantarflexion resistance spring recruitment angle and is in contact with the plantarflexion resistance transmission member.

23. The device of claim 1 wherein the terminal stance dorsiflexion resistance spring is selected from the group consisting of a wire spring, a polyurethane spring, a machined spring and a gas spring.

24. The device of claim 1 wherein the initial dorsiflexion resistance spring is a helical wire spring, the terminal stance dorsiflexion resistance spring is a wire spring, and the initial dorsiflexion resistance spring and terminal stance dorsiflexion resistance spring are in parallel.

25. The device of claim 1 wherein the dorsiflexion resistance springs provide a dorsiflexion resistance that increases abruptly as the dorsiflexion angle increases and passes through the terminal stance dorsiflexion resistance spring recruitment angle.

* * * * *